US012232943B2

(12) United States Patent
Sengun et al.

(10) Patent No.: US 12,232,943 B2
(45) Date of Patent: Feb. 25, 2025

(54) SYSTEMS AND METHODS FOR USING STRUCTURED TISSUE AUGMENTATION CONSTRUCTS IN SOFT TISSUE FIXATION REPAIR

(71) Applicant: Medos International Sàrl, Le Locle (CH)

(72) Inventors: Mehmet Ziya Sengun, Canton, MA (US); Douglas L. Hester, Dartmouth, MA (US); Tamim Diab, Attleboro, MA (US)

(73) Assignee: Medos International Sàrl, Le Locle (CH)

( * ) Notice: Subject to any disclaimer, the term of this patent is extended or adjusted under 35 U.S.C. 154(b) by 633 days.

(21) Appl. No.: 17/243,179

(22) Filed: Apr. 28, 2021

(65) Prior Publication Data

US 2022/0346926 A1 Nov. 3, 2022

(51) Int. Cl.
*A61F 2/00* (2006.01)
*A61F 2/08* (2006.01)
*A61L 31/04* (2006.01)

(52) U.S. Cl.
CPC .......... *A61F 2/0063* (2013.01); *A61F 2/0811* (2013.01); *A61F 2002/0072* (2013.01); (Continued)

(58) Field of Classification Search
CPC .................. A61F 2/0063; A61F 2/0811; A61F 2002/0072; A61F 2002/0852; (Continued)

(56) References Cited

U.S. PATENT DOCUMENTS 5,366,460 A * 11/1994 Eberbach .............. A61F 2/0063
606/1
5,514,378 A 5/1996 Mikos et al.
(Continued)

FOREIGN PATENT DOCUMENTS

EP 0464163 A1 1/1992
EP 3412218 A1 12/2018
(Continued)

OTHER PUBLICATIONS

Extended European Search Report for Application No. 22170220 issued Jan. 27, 2023 (9 pages).
(Continued)

*Primary Examiner* — Brian A Dukert
*Assistant Examiner* — Rebecca Lynee Zimmerman
(74) *Attorney, Agent, or Firm* — Barnes & Thornburg LLP

(57) ABSTRACT

Devices, systems, and methods to improve both the reliability of soft tissue repair procedures and the speed at which the procedures are completed are provided. The devices and systems include one or more structured tissue augmentation constructs, which include constructs that are configured to increase a footprint across which suture applied force to tissue when the suture is tied down onto the tissue. The tissue augmentation constructs can be quickly and easily associated with the repair suture and can be useful in many different tissue repair procedures that are disclosed in the application. The present disclosure includes structured tissue augmentation blocks for tendon repair that have a flexible or semi-flexible skeleton integrated into the block. The skeleton can be bioabsorbable and can create both in-plane and out-of-plane curvature in the block.

19 Claims, 17 Drawing Sheets

(52) U.S. Cl.
CPC .............. *A61F 2002/0852* (2013.01); *A61F 2210/0004* (2013.01); *A61F 2230/0013* (2013.01); *A61L 31/044* (2013.01)

(58) Field of Classification Search
CPC ..... A61F 2210/0004; A61F 2230/0013; A61L 31/044
See application file for complete search history.

(56) References Cited

U.S. PATENT DOCUMENTS

| | | | |
|---|---|---|---|
| 5,824,082 | A | 10/1998 | Brown |
| 6,599,323 | B2 | 7/2003 | Melican et al. |
| 6,626,916 | B1 | 9/2003 | Yeung et al. |
| 7,368,124 | B2 | 5/2008 | Chun et al. |
| 8,562,633 | B2 | 10/2013 | Cully et al. |
| 8,690,960 | B2 | 4/2014 | Hotter et al. |
| 9,345,567 | B2 | 5/2016 | Sengun |
| 9,398,943 | B2 | 7/2016 | Criscuolo et al. |
| 2007/0190108 | A1 | 8/2007 | Datta et al. |
| 2010/0152530 | A1 | 6/2010 | Timmer et al. |
| 2010/0168864 | A1 | 7/2010 | White et al. |
| 2011/0077457 | A1* | 3/2011 | Deitch .................. A61F 2/0045 600/37 |
| 2017/0143551 | A1* | 5/2017 | Coleman ............... A61F 2/0063 |
| 2017/0215864 | A1 | 8/2017 | Sengun et al. |
| 2017/0273680 | A1 | 9/2017 | Sengun et al. |
| 2020/0000573 | A1 | 1/2020 | Whittaker et al. |
| 2020/0015962 | A1 | 1/2020 | Detamore et al. |
| 2021/0369276 | A1* | 12/2021 | Ou .......................... A61L 24/02 |

FOREIGN PATENT DOCUMENTS

| | | | |
|---|---|---|---|
| EP | 3753497 | A1 | 12/2020 |
| WO | WO-2014070896 | A1 * | 5/2014 ......... A61L 27/3633 |

OTHER PUBLICATIONS

Young, "Microcellular Foams via Phase Separation", J. Vac. Sci. Technol., vol. 4(3), Jun. 1986.

* cited by examiner

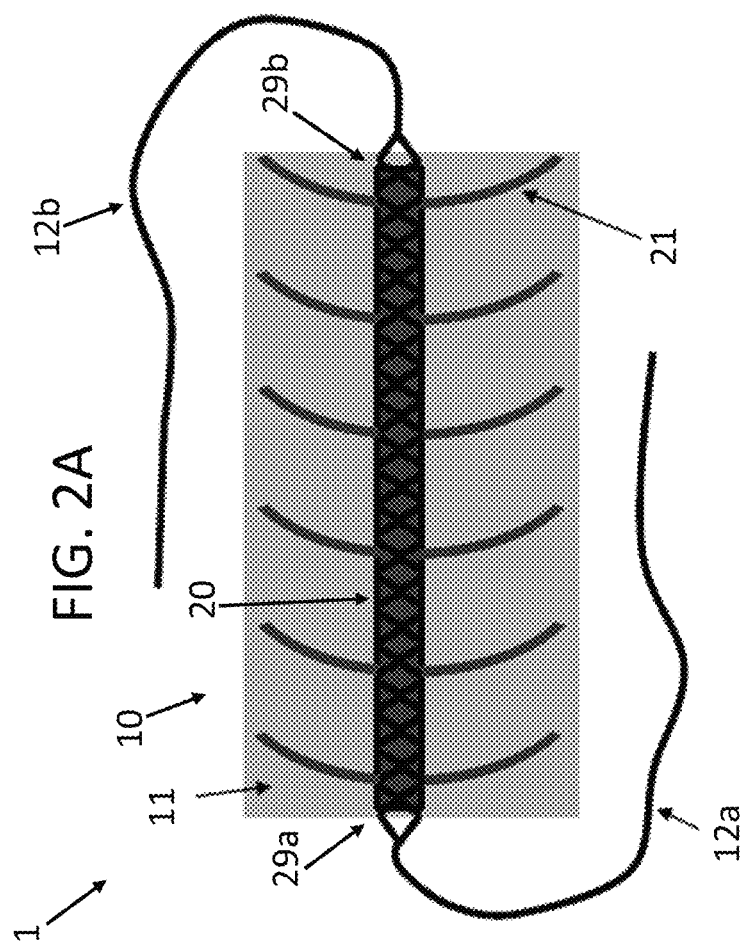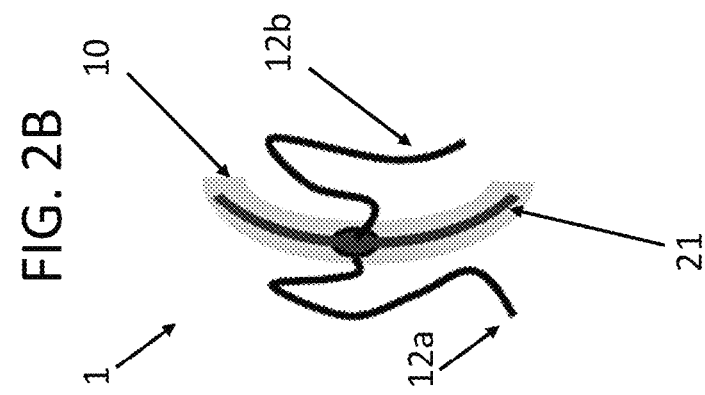

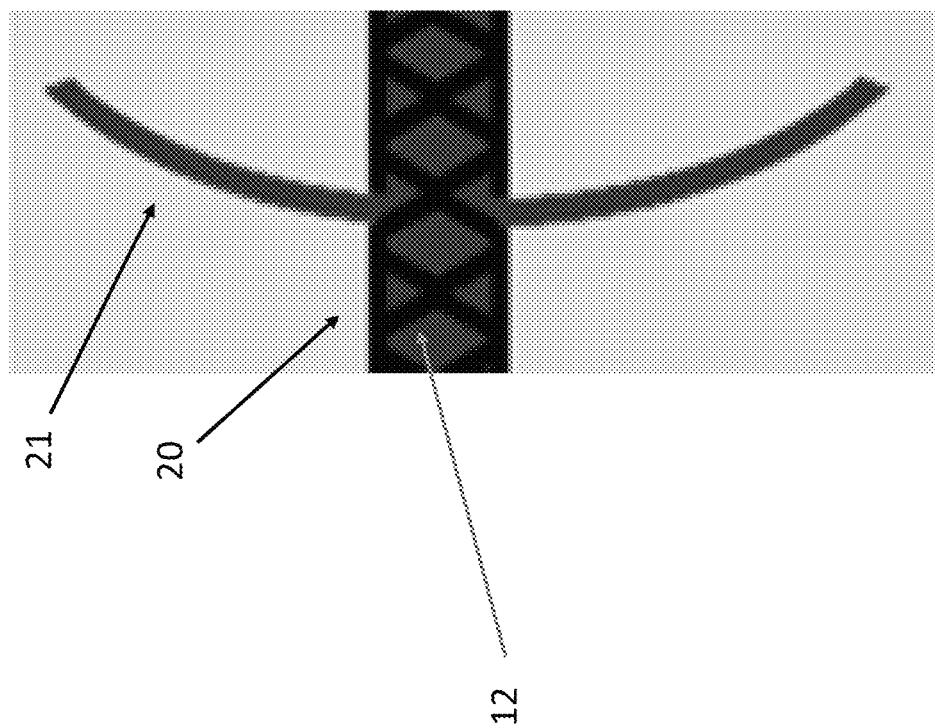

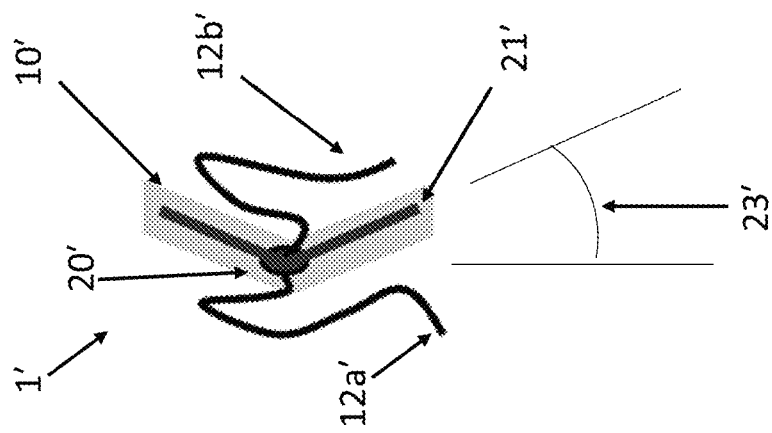
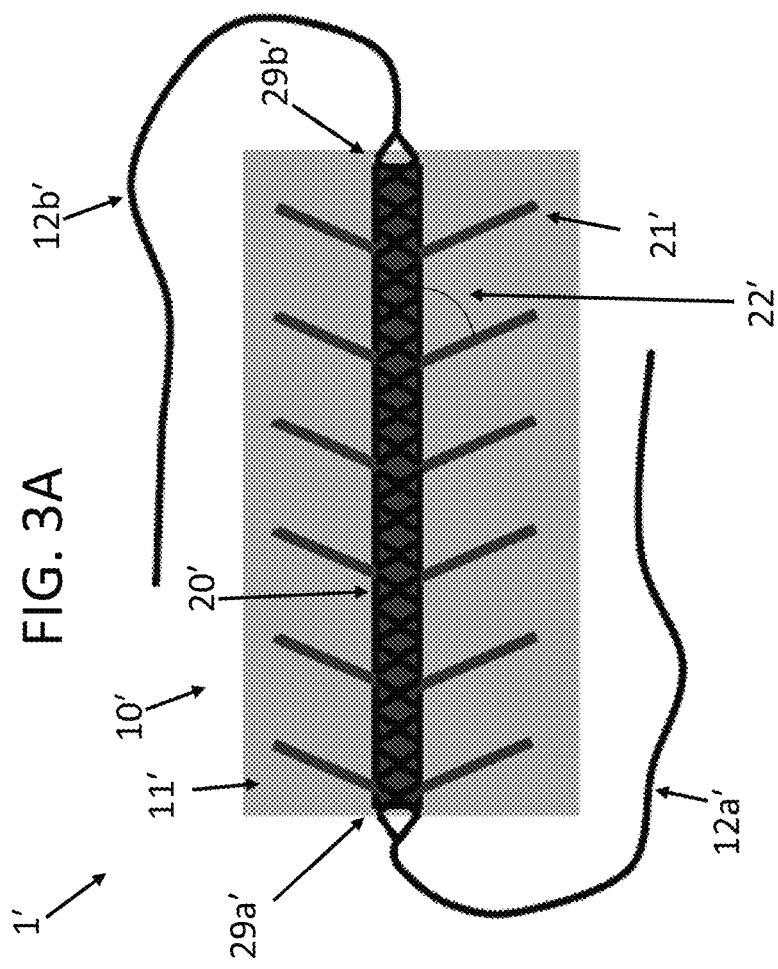

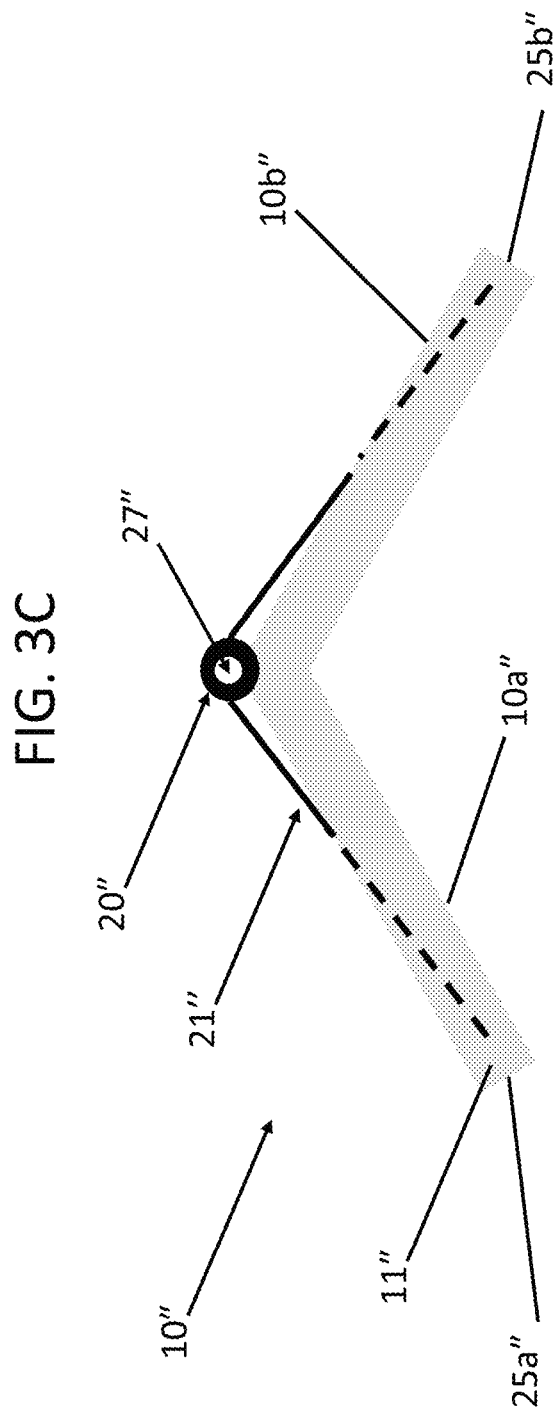

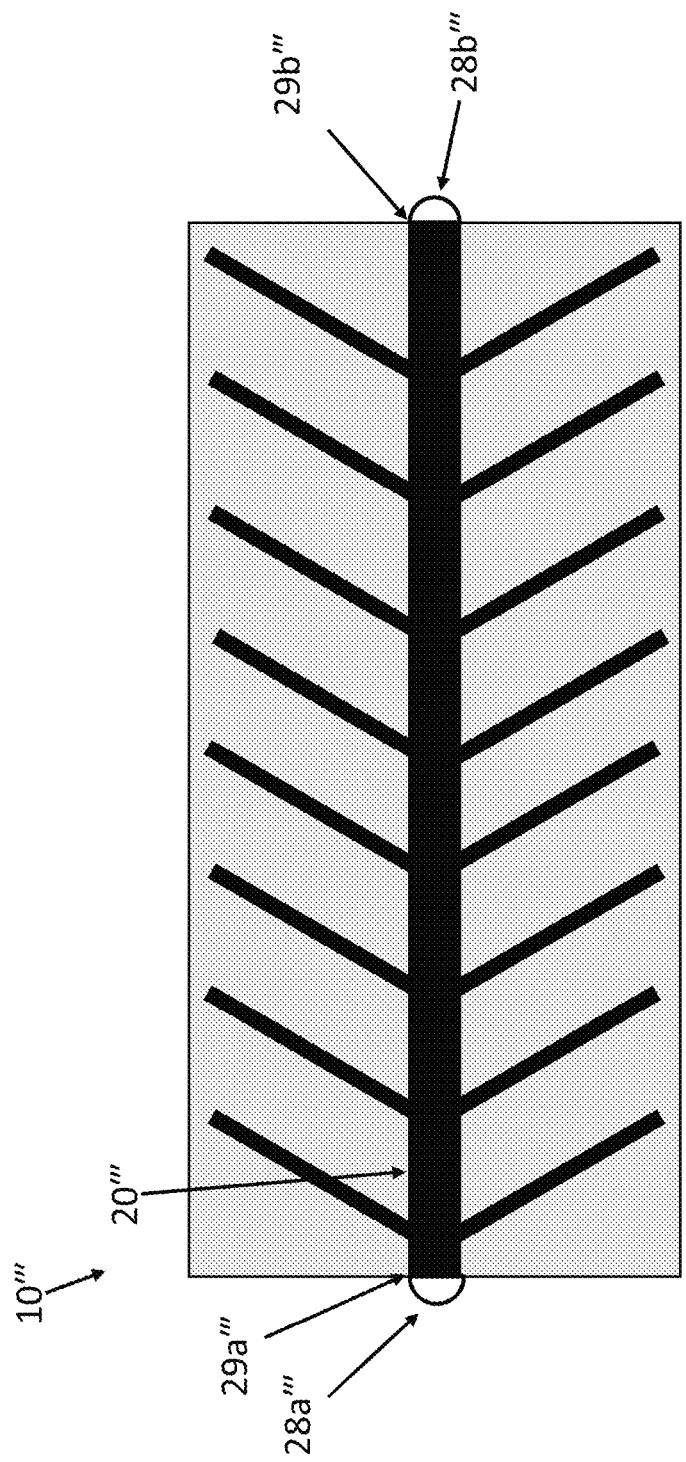

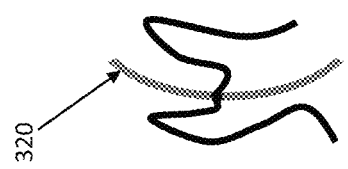
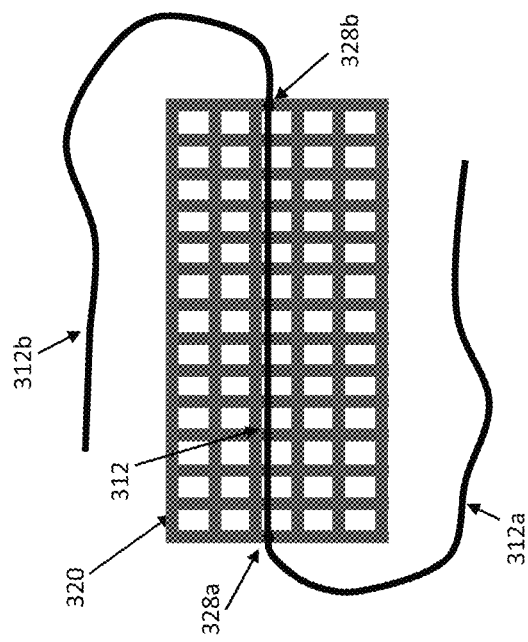

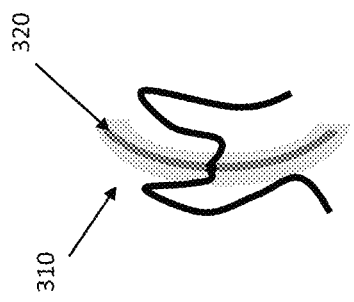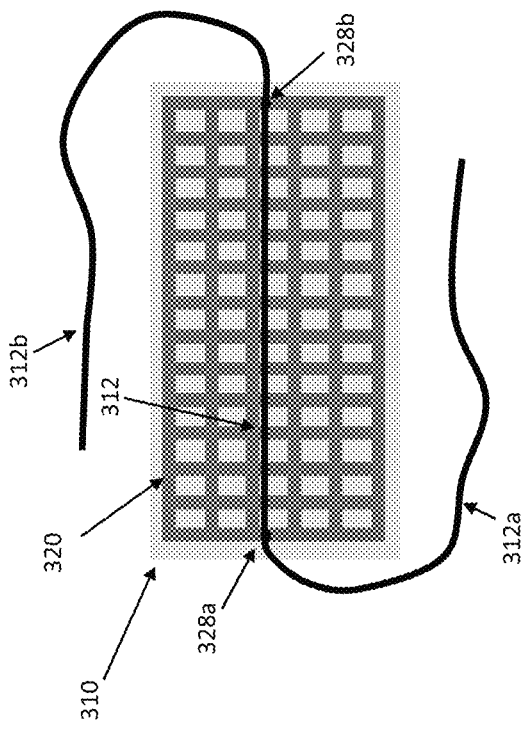

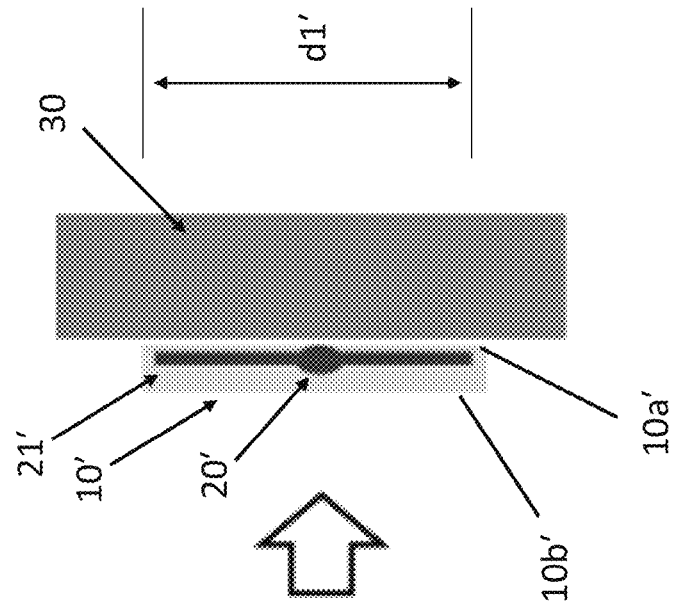
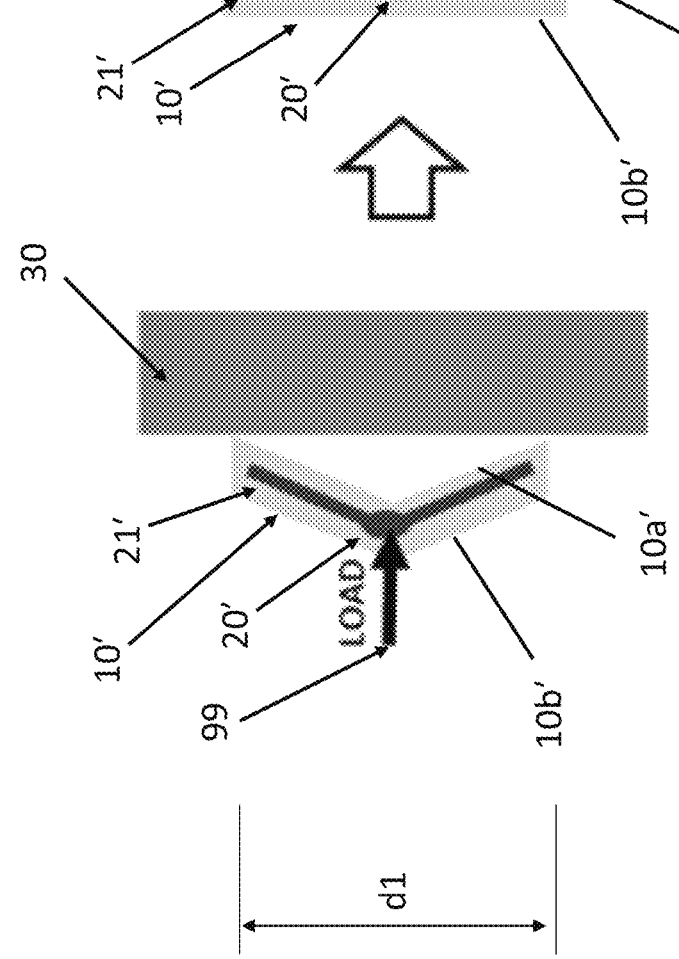

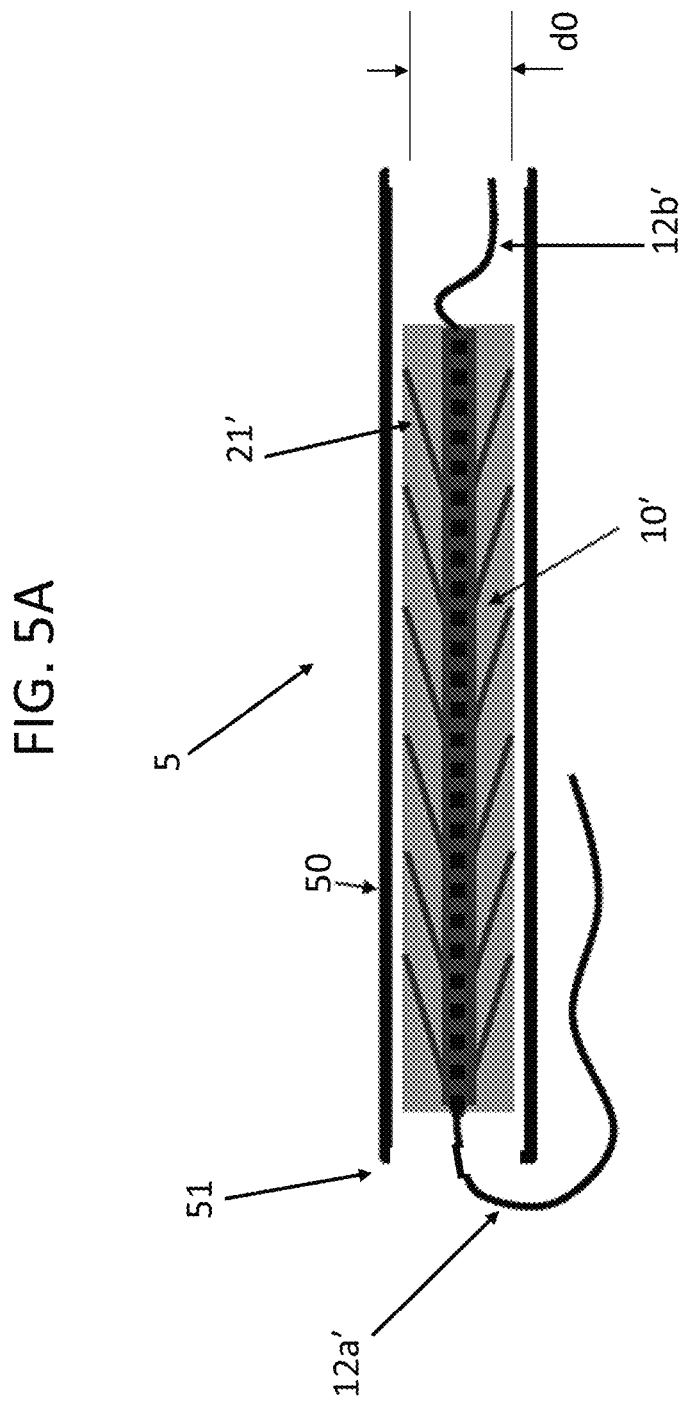

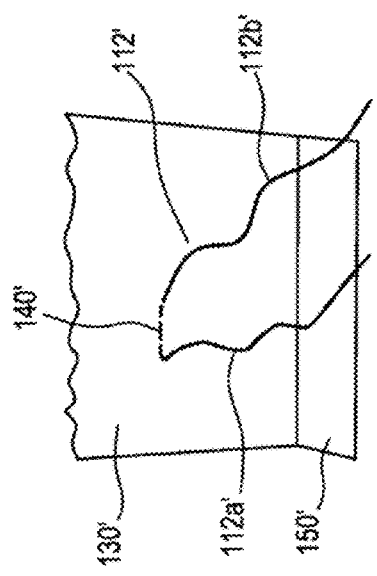
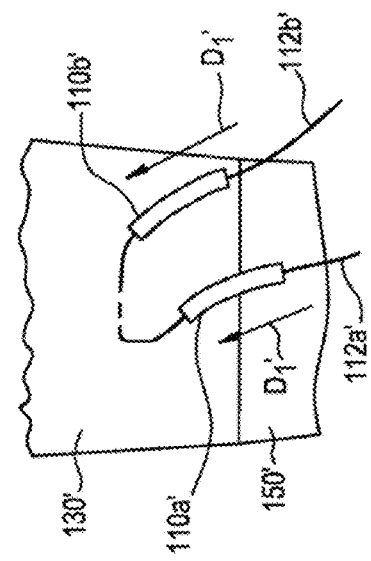
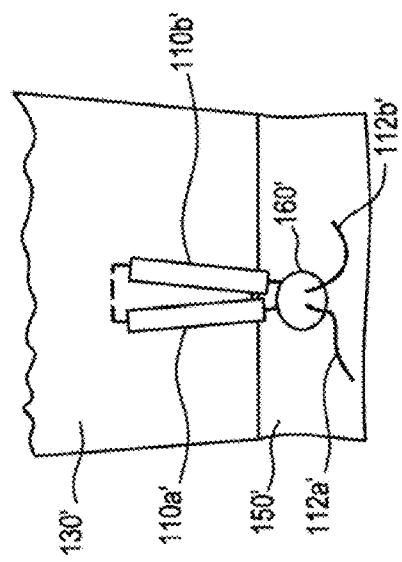

SYSTEMS AND METHODS FOR USING STRUCTURED TISSUE AUGMENTATION CONSTRUCTS IN SOFT TISSUE FIXATION REPAIR

FIELD

The present disclosure relates to systems, devices, and methods for securing soft tissue to bone, and more particularly relates to systems, devices, and methods that include a structured tissue augmentation patch that simplifies surgical techniques and improves outcomes.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to degenerated tissue leading to inadequate suture-to-anchor fixation and further damage to the soft tissue.

Repair constructs made from one or more surgical filaments are typically used in soft tissue repair procedures, e.g., rotator cuff fixations, to secure the tissue in a desired location. The repair constructs are typically disposed through one or more portions of the tissue to be repaired, which can cause trauma to the tissue, and are often coupled to anchors disposed in bone to which the tissue is to be approximated. Further, in situations where the soft tissue has already begun to degenerate, the added pressure applied by the sutures can cause further damage to the tissue, for instance by causing abrasion of the tissue or "cheese-wiring," which refers to one or more strings of tissue peeling away from the main tissue like a string of cheese peels away from a cheese block when a wire cheese slicer is used to separate cheese from the block. In other words, because the suture has a small surface area, and a significant amount of force is being applied to the soft tissue over the small surface area of the tissue, the suture may have a tendency to cut into the already compromised tissue, thus causing further damage. Currently available solutions to this problem include the application of a relatively large formation of allograft or xenograft, typically about 3 centimeters by about 3 centimeters, to the soft tissue after the repair has been performed but prior to tightening the soft tissue down with the suture. The application of the formation, however, is often expensive, necessitates many sutures, and requires a high skill level to operate and is thus used by only a select few surgeons. Further, the application of the relatively large formation can add a significant amount of time to a surgical procedure, on the order of an additional half hour to one hour per allograft or xenograft formation applied. Still further, in certain forms of repair constructs, such as those that include a membrane that provides strength to the repair construct, it can be difficult for a surgeon to ensure a preferred side of the repair construct is in contact with the host tissue.

Additionally, repair constructs, such as patches or scaffolds as provided for herein, can sometimes be cumbersome to deliver. The delivery occurs through a small opening or cannula, often causing the construct to be deformed prior to and/or during insertion to the surgical site. Existing repair operations can involve delivery of a tissue augmentation patch or scaffold through a small opening or cannula into the surgical region. Passing the tissue augmentation patch through the small opening can be difficult and often requires the tissue augmentation patch to be deformed prior to and/or during insertion. Still further, methods that employ a surgical repair construct often involve first performing the surgical repair, e.g., a rotator cuff repair, and then subsequently inserting the surgical repair construct. The associated techniques disrupt surgical workflow, lengthening the time for performing the procedure, among other drawbacks caused by separating out these events, such drawbacks being evident to those skilled in the art.

Additionally, despite years of development and improvements, some soft tissue repairs, such as rotator cuff repair, are still subject to failure due to insufficient healing, especially for large and massive tears. Therefore, there is a clinical need for an improved repair technique. One such improvement is provided by covering the repair site with a biologically active patch. Ideally, the approach would provide an easy and speedy delivery with robust and reproducible arthroscopic fixation, which is an unmet need at present.

It is therefore desirable to provide systems, devices, and methods for use in soft tissue repair that are robust, strong, and promote healing, yet minimize the costs and time of the procedure and provide for easier delivery of surgical repair constructs provided for herein (e.g., tissue augmentation patches) to the surgical site.

SUMMARY

Systems, devices, and methods are generally provided for performing surgical procedures involving sutures, such as rotator cuff repairs, among other suture repair procedures. More specifically, the systems, devices, and methods include one or more structured tissue augmentation constructs or matrices being used to perform the tissue repair. The structured tissue augmentation constructs, which come in a variety of configurations, including but not limited to tapes, blocks, tacks, and patches, can expand a footprint of the sutures with which they are associated. The expanded footprint helps distribute force applied by the suture on the tissue across a greater surface area, can protect aspects of the system and/or tissue, provide bulk to otherwise compromised or degenerate tissue and/or tendon, and can help promote tissue growth and repair at the surgical site.

The structured tissue augmentation constructs can include integrated suture(s) so that a surgeon can quickly and easily conduct the soft tissue repair with leads extending from the integrated suture or quickly tie tails of the integrated suture to existing lengths of suture already in use to conduct the repair, or similarly purposed materials such as suture tape, being used based on the needs presented during the procedure. Surgical procedures that utilize the structured tissue augmentation constructs provided for in the present disclosure are also described.

Examples of the present disclosure include a structured tissue augmentation system for tendon repair, such as rotator cuff repair, and methods for arthroscopic delivery and fixation of the structured tissue augmentation system. In some examples, a flexible or semi-flexible skeleton is integrated into a flexible and biologically active tissue augmentation construct and partially- or fully-encapsulated by the flexible and biologically material of the tissue augmentation construct. Examples of this integration include layer-by-layer deposition or by molding of tissue augmentation material around the skeleton. In some examples, the tissue augmentation construct materials include collagen or reconstituted collagen.

The skeleton can be made from a biocompatible (including bioabsorbable) material and can be arranged as a central spine with multiple lateral wings extending from the central spine in a mostly-sideways direction (e.g., towards a lateral side edge of the tissue augmentation construct). A list of such materials includes polyetheretherketone (PEEK), polyethylene terephthalate (PET), polypropylene, PDS, Monocryl, etc., or a combination. From a top-down perspective (e.g., observing the major plane of the tissue augmentation construct), the lateral wings extending from the central spine may have a biased orientation longitudinally (e.g., resembling a fish bone). From an end view (e.g., observing the thickness of the tissue augmentation construct), the wings can also be oriented or curved towards one side such that, in a free state, the overall structured tissue augmentation construct is not planar but has a curved or semi-folded geometry. Accordingly, if the structured tissue augmentation construct is pressed towards a rigid surface by pushing on the central spine, the wings can be forced to spring open to maintain full contact between the structured tissue augmentation construct and the surface.

The structured tissue augmentation construct can be managed and manipulated during a surgical procedure by suture tails either attached to ends of the spine and/or by suture that is over-braided along the central spine of the skeleton.

The structured tissue augmentation construct can be disposed in a delivery tube in a collapsed state, with the flexibility of the wings of the skeleton allowing the structured tissue augmentation construct to be constricted through a small diameter by flexing the wings towards the central spine. During an example delivery and fixation operation, a distal suture extending from the skeleton of the structured tissue augmentation construct disposed in a delivery tube can be first passed through a medial location in soft tissue to tie the distal end of the skeleton at that point. The delivery tube can then be retracted, allowing collapsed wings of the structured tissue augmentation construct to spring open as the structured tissue augmentation construct is removed from the delivery tube, thereby spreading the structured tissue augmentation construct laterally back to a free state. Thereafter, a proximal suture limb attached to a proximal end of the skeleton can be fixated to a bone and used to tighten the structured tissue augmentation construct against the soft tissue such that the structured tissue augmentation construct is spring-loaded against the soft tissue.

An example of the present disclosure is a structured surgical construct that includes a tissue augmentation block and a support skeleton at least partially integrated with the tissue augmentation block such that flexing of the tissue augmentation block induces a corresponding flexing of at least a portion of the support skeleton. The tissue augmentation block has a first tissue-engaging surface with a surface area defined by a length and a width of the block and a second surface with a surface area defined by the length and the width of the block. The second surface is opposed to the first tissue-engaging surface and a thickness of the block is defined by a distance between the first tissue-engaging surface and the second surface. The surface areas of the first tissue-engaging surface and the second surface are larger than the surface areas of any other sides of the block, and the thickness is the shortest of the length, the width, and the thickness of the block. The support skeleton is configured such that it is biased in an expanded configuration that in turn causes the tissue augmentation block to expand.

The support skeleton can have a monolithic construction. The support skeleton can be at least partially encapsulated by the tissue augmentation block. In some examples, the support skeleton is fully encapsulated by the tissue augmentation scaffold. The support skeleton can be made from a bio-absorbable material. In some embodiments, the block can include at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia. In some instances, the tissue augmentation block can include collagen.

The structured surgical construct can include a suture coupled at a first end of the support skeleton. The suture can be coupled at a second end of the support skeleton. The support structure can include a plurality of elements in at least one of a lattice arrangement or a mesh arrangement.

In some examples, the support skeleton further includes a spine and a plurality of ribs. The spin can extend along at least a portion of the length of the block. The plurality of ribs can include a plurality of first ribs that extend from the spine along the width of the block in a first direction towards a first end of the block, and a plurality of second ribs that extend from the spine along the width of the block in a second direction towards a second end of the block. A distance between the first and second ends of the block can define the width of the block. The plurality of first and second ribs can be coupled with the tissue augmentation block such that flexing of the first and second ends of the block about the spine induces a corresponding flexing of the plurality of first and second ribs about the spine. The plurality of first and second ribs can be curved such that the tissue augmentation block is curved with respect to a longitudinal axis of the spine. The first tissue-engaging surface can be concave along the length of the tissue augmentation block in the expanded configuration. The first tissue-engaging surface can be flexed against a surface to a less concave orientation by applying a force to the spine in a direction towards the surface. In some instances, at least a portion of the plurality of first ribs and at least a portion of the plurality of second ribs extend in non-diametrically opposed directions about a plane perpendicular to the spine such that at least a first lateral portion of the tissue augmentation block is bent about the spine in the plane perpendicular to the spine with respect to a second lateral portion. In some instances, the plurality of first and second ribs are at least one of curved or angled towards a same end of the spine such that the tissue augmentation block is configured to be constricted by deflection of the plurality of first and second ribs towards the spine. In some instances, the central spine defines a central lumen.

The structured surgical construct can include a suture coupled at a first end of the spine. The suture can extend along at least a portion of the spine. The suture can be braided along at least a portion of the spine.

The structured surgical construct can include a suture braided along the spine, the suture having a first tail extending from a first end of the spine and a second tail extending from a second end of the spine.

Another example is a surgical kit that includes a structured tissue augmentation construct, a suture, and delivery tube. The structured tissue augmentation construct includes a first tissue-engaging surface with a surface area defined by a length and a width of the construct and a second surface with a surface area defined by the length and the width of the construct. The second surface is opposed to the first tissue-engaging surface and a thickness of the construct is defined by a distance between the first tissue-engaging surface and the second surface. The surface areas of the first tissue-engaging surface and the second surface are larger than the surface areas of any other sides of the construct, and the thickness is the shortest of the length, the width, and the thickness of the construct. The structured tissue augmentation construct further includes a support skeleton at least partially integrated with the tissue augmentation construct such that flexing of the construct induces a corresponding flexing of at least a portion of the support skeleton. The support skeleton is configured such that it is biased in an expanded configuration that in turn causes the structured tissue augmentation construct to expand. The suture is integrated with the support skeleton, with the suture including a first tail configured to extend from a first longitudinal end of the construct, and a second tail configured to extend from a second longitudinal end of the construct. The delivery tube is configured to contain the structured tissue augmentation construct in a constricted arrangement.

In some examples, the support skeleton includes a spine extending along at least a portion of the length of the construct, a plurality of first ribs extending from the spine along the width of the construct in a first direction towards a first lateral end of the construct, and a plurality of second ribs extending from the spine along the width of the construct in a second direction towards a second lateral end of the construct. The plurality of first and second ribs can be coupled with the tissue augmentation construct such that flexing of the first and second ends of the construct about the spine induces a corresponding flexing of the plurality of first and second ribs about the spine. In the constricted arrangement, the plurality of first and second ribs can be deflected towards the spine.

In some examples, the suture is braided around the central spine. The plurality of first and second ribs can be curved such that the tissue augmentation block is curved with respect to a longitudinal axis of the spine. At least a portion of the plurality of first ribs and at least a portion of the plurality of second ribs can extend in non-diametrically opposed directions about a plane perpendicular to the spine such that at least a first lateral portion of the tissue augmentation block is bent about the spine in the plane perpendicular to the spine with respect to a second lateral portion. In some examples, the plurality of first and second ribs are at least one of curved or angled towards a same end of the spine such that the structured tissue augmentation construct is configured to be constricted by deflection of the plurality of first and second ribs towards the spine. The support skeleton can include a bio-absorbable material (e.g., collagen). The support skeleton can be curved such that the first tissue-engaging surface is concave.

In some examples, the first tissue-engaging surface can be flexed against a surface to a less concave orientation by applying a force to skeleton towards the surface via the suture.

Yet another example of the present disclosure is surgical method of repairing soft tissue. The method includes attaching a first suture limb to soft tissue. The first suture limb extends from a distal end of a structured tissue augmentation construct having a support skeleton at least partially disposed in the construct. The support skeleton defines a resting concave curvature along a longitudinal length of a tissue-engaging surface of the structured tissue augmentation construct. The method further includes coupling a second suture limb that extends from a proximal end of the structured tissue augmentation construct to a suture anchor disposed in bone, and tightening one or both of the first and second suture limbs such that the tissue-engaging surface of the structured tissue augmentation construct is urged against the soft tissue and the support skeleton is at least partially deflected by the soft tissue such that the concave tissue-engaging surface is splayed against the tissue and held in the splayed position by the tightening of the one or both of the first and second the suture limbs.

The support skeleton can include at least one of a lattice structure or a mesh structure. The support skeleton can includes a central spine and a plurality of first and second ribs extending in opposite directions along a width of the structured tissue augmentation construct. The first and second ribs can define a resting concave curvature along a longitudinal length of the tissue-engaging surface of the structured tissue augmentation construct, and the plurality of first and second ribs can be deflected when the tissue-engaging surface of the structured tissue augmentation construct is urged against the soft tissue. The deflecting can reduce the concave curvature.

The method can further include removing the structured tissue augmentation construct from a delivery tube. In some such embodiments, before removal from the delivery tube, the structured tissue augmentation construct can be constricted along the longitudinal length such that the plurality of first and second ribs are held in a deflected position towards the spine by the delivery tube. Removing the structured tissue augmentation construct can include releasing the plurality of first and second ribs such that the resting concave curvature of the tissue-facing surface is restored.

In some examples, the structured tissue augmentation construct is held in the delivery tube such that the central spine is substantially aligned with a central axis of the delivery tube. In some examples, attaching a first suture limb to soft tissue includes installing a medial row stitch. In some such embodiments, coupling the second suture limb with the suture anchor disposed in bone further can include installing a lateral row fixation.

The structured tissue augmentation construct can include at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia. In some embodiments, the structured tissue augmentation construct can include collagen.

The method can further include attaching the first suture limb to a distal end of the support skeleton of the structured tissue augmentation construct. The method can further include attaching the second suture limb to a proximal end of the support skeleton of the structured tissue augmentation construct. The method can further include passing the first or second suture limb through a lumen in the support skeleton.

Unless otherwise specified, such as instances in which advantages are described related to delivering a tissue augmentation construct to a surgical repair site prior to performing the repair, the steps of the methods provided for in the present disclosure can be performed in any order.

BRIEF DESCRIPTION OF DRAWINGS

FIG. 2A is a top view of an exemplary embodiment of the structured tissue augmentation construct of FIG. 1A;

FIG. 2B is an end view of the structured tissue augmentation construct of FIG. 2A;

FIG. 2C is a detailed top view of the suture braided over a central spine of the structured tissue augmentation construct of FIG. 2A;

FIG. 3A is a top view of another exemplary embodiment of a structured tissue augmentation construct;

FIG. 3B is an end view of the structured tissue augmentation construct of FIG. 3A;

FIG. 3C is an end view of yet another exemplary embodiment of a structured tissue augmentation construct;

FIG. 3D is a top view of still another exemplary embodiment of a structured tissue augmentation construct;

FIG. 3E is a top view of an exemplary embodiment of a lattice skeleton structure;

FIG. 3F is an end view of the lattice skeleton structure of FIG. 3E;

FIG. 3G is a top view of a structured tissue augmentation construct made with the lattice skeleton structure of FIG. 3D;

FIG. 3H is an end view of the structured tissue augmentation construct of FIG. 3G;

FIGS. 4A and 4B are end views the structured tissue augmentation construct of FIG. 3A being disposed against soft tissue during a surgical procedure;

FIG. 5A is an illustration of the structured tissue augmentation construct of FIG. 3A disposed in a delivery tube;

FIGS. 7A-7C are schematic sequential views of one exemplary embodiment for installing multiple structured tissue augmentation constructs in a single row fixation;

DETAILED DESCRIPTION

Figure 1A:
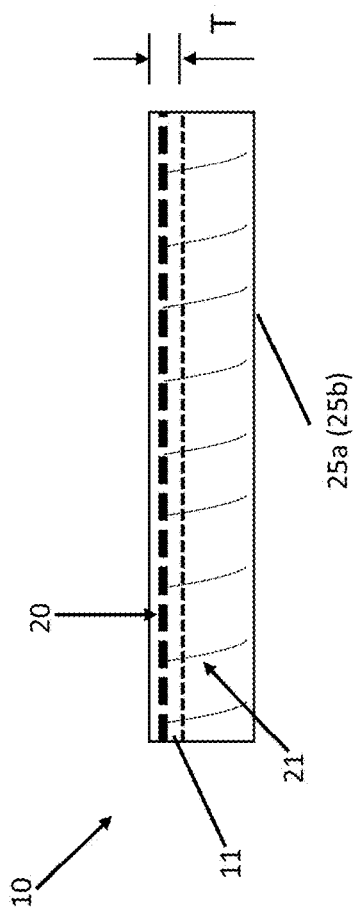
FIG. 1A is a top view of one exemplary embodiment of a structured tissue augmentation construct.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction of movement, these arrows are illustrative and in no way limit the direction the respective component can or should be moved. A person skilled in the art will recognize other ways and directions for creating the desired result in view of the present disclosure. Additionally, a number of terms may be used throughout the disclosure interchangeably but will be understood by a person skilled in the art. By way of non-limiting example, the terms suture, filament, and flexible members may be used interchangeably, and includes other similarly purposed materials, such as suture tape. Further, to the extent the term "block" is used to describe some of the constructs and matrices provided for herein, the constructs and matrices are not limited to a square or a rectangle, or any shape having flat surfaces for that matter. Still further, to the extent the term "thread" is used to describe associating one component with another, the term is not limited to mean actually passing filament through another material. It can also include passing it through an opening (e.g., an opening formed in a body, as described below at least with respect to some tissue augmentation blocks), and thus can more generally mean associating one component with another. To the extent "features" or "step orders" are described as being a "first feature" or "first step," or a "second feature" or "second step," such ordering is generally arbitrary, unless specifically indicated otherwise, and thus such numbering can be interchangeable.

Systems, devices, and methods for soft tissue repair are generally provided, with such systems or devices including but not being limited to one or more structured tissue augmentation constructs, which include strips, bars, and/or patches, and which are described in greater detail below. As described herein, the term "construct" refers to any implant associated with suture limbs to expand the footprint of the limb. Surgical repair filaments or flexible members can come in a variety of configurations including in typical suture configurations and tape forms, and can be used in connection with a variety of types of suture implants, e.g., filament anchors, suture anchors, or bone anchors, including hard and soft anchors, to attach or reattach soft tissue to bone. The repair filaments can pass through soft tissue so that the soft tissue can be positioned in a desired location. The repair filaments are secured to anchors which, in turn, are fixed in bone. The structured tissue augmentation construct(s) can be incorporated with or associated with the surgical repair filaments to increase coverage and bulk to compromised or degenerate soft tissue, to increase a surface area along which compression between the suture repair filament and tissue being repaired is applied, and to help promote tissue growth and repair. While each of the repair filament, structured tissue augmentation construct, and suture implant is described as being part of the systems or devices, any one component can be provided for separately for use with the other components or other implants and devices used in surgical procedures.

While many different repair procedures can be enhanced by the present disclosures, in some exemplary embodiments the soft tissue repair devices and systems provided for herein can be used for rotator cuff fixation procedures. In rotator cuff fixation procedures a surgeon can reattach the rotator cuff to the bone by first threading a suture through the soft tissue such that two suture limbs extend from the tissue. The surgeon can thread or otherwise attach each of the suture limbs through respective structured tissue augmentation constructs, and subsequently fix the suture limbs to one or more bone anchors proximate to the tissue.

In other examples, the structured tissue augmentation constructs include integrated suture limbs extending from an over-braided central spine of a flexible skeleton structure of the structured tissue augmentation constructs. The structured tissue augmentation constructs increase the surface area, or footprint, of the system that contacts the soft tissue. This enlarged footprint may disperse any loading forces on the soft tissue, and, as a result, the tensioned suture may be less likely to abrade or otherwise damage the soft tissue, for instance by "cheese wiring." Moreover, the structured tissue augmentation constructs can be easily and quickly threaded onto or otherwise associated with suture limbs during the procedure, which contrasts from existing systems that involved complicated, time-intensive approaches for associating xenograft or allograft formations with suture limbs, or can include suture limbs extending from a length of suture integrated with a flexible skeleton of the structured tissue augmentation constructs. The resulting procedures thus allow for the structured tissue augmentation constructs to be added onto suture limbs in an on-demand fashion or provide pre-integrated suture limbs for use during a surgical procedure.

Still further, the structured tissue augmentation constructs can be made from biocompatible materials (e.g., collagen), among other types of materials, such that during healing new bands of tissue growth can occur, further increasing the efficacy of the rotator cuff fixation procedure, which includes the flexible skeleton being also constructed from biodegradable materials In other non-limiting exemplary embodiments disclosed herein, the soft tissue repair devices and systems can be used in other soft tissue repair procedures for example, repair of torn anterior cruciate ligament (ACL), instability or glenoid procedures, meniscal repair, superior capsule reconstruction, and hip capsular closure, among others. Various methods of using installation tools to deliver structured tissue augmentation constructs into an operative environment are also described.

Additional details about tissue augmentation constructs are provided in U.S. patent application Ser. No. 15/419,330, entitled "TISSUE AUGMENTATION CONSTRUCTS FOR USE WITH SOFT TISSUE FIXATION REPAIR SYSTEMS AND METHODS," and filed Jan. 30, 2017, and as well as in U.S. patent application Ser. No. 16/445,930, entitled "TISSUE AUGMENTATION SCAFFOLDS FOR USE IN SOFT TISSUE FIXATION REPAIR," and filed Jun. 19, 2019, the contents of both of which are incorporated by reference herein in their entirety. Additional details about tissue augmentation tacks suitable for use with aspects of the present disclosure are provided in U.S. patent application Ser. No. 15/618,984, entitled "TISSUE AUGMENTATION TACKS FOR USE WITH SOFT TISSUE FIXATION REPAIR SYSTEMS AND METHODS," and filed Jun. 9, 2018, the content of which is incorporated by reference herein in its entirety.

Structured Tissue Augmentation Constructs Having a Strip or Tape Configuration

Figure 1B:
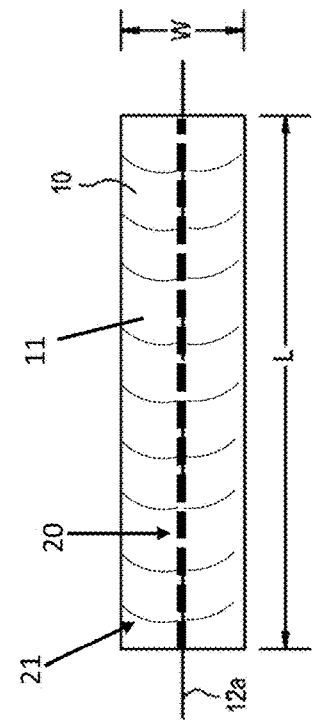
FIG. 1B is a side view of the structured tissue augmentation construct of FIG. 1A.
Figure 1C:
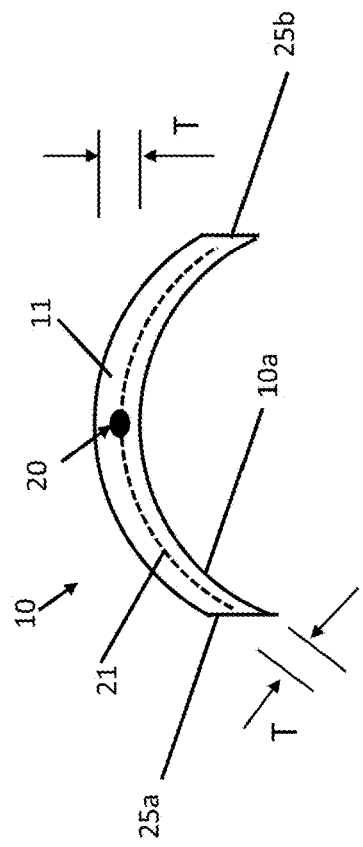
FIG. 1C is an end view of the structured tissue augmentation construct of FIG. 1A.

One exemplary embodiment of a structured tissue augmentation construct, as shown a structured tissue augmentation construct 10, is provided for in FIGS. 1A-1C. In one exemplary embodiment, the structured tissue augmentation construct 10 is a strip or tape configured with an integrated suture limb 12a or configured to otherwise be threaded onto or associated with the suture limb 12a. More particularly, the structure tissue augmentation construct 10 can have a substantially rectangular shape with a width W, length L, and thickness T, and includes a substantially curved, tissue-engaging surface 10a and an opposite surface 10b. In operation, the structured tissue augmentation construct is pressed against a soft tissue and the curve in the tissue-engaging surface 10a is undone as the tissue-engaging surface 10a is urged into a flat or substantially flat orientation when held against the soft tissue by sutures, as explained in more detail below. As shown, the structured tissue augmentation construct 10 is longer than it is wide and wider than it is thick. Typically the length L is substantially greater than the width W and the width W is substantially greater than the thickness T. Further, the width W can be greater than a diameter of a filament or suture with which the tissue augmentation tape 10 is associated, e.g., the suture limb 12a, thereby increasing the surface area of compression of the system or device used in the surgical repair.

The structured tissue augmentation construct 10 includes a tissue augmentation material 11, which defines the primary shape and dimension of the structured tissue augmentation construct 10 and can also be referred to herein as a tissue augmentation block, and it includes an internal flexible skeleton structure that can be wholly or partially encapsulated by the tissue augmentation material 11. The skeleton includes a spine 20 that, as illustrated, extends along substantially all of the length L of the tissue augmentation material 11, and from the central spine 20 a plurality of flexible lateral wings 21 extend through the tissue augmentation material 11 towards the lateral edges 25a, 25b (e.g., the ends defining the width W). The flexible lateral wings 21 can be curved in both the primary plane of the tissue augmentation material 11 (as shown in FIG. 1A), as well as curved out of the primary plane (as shown in FIGS. 1B and 1C). The out of plane curvature of the flexible lateral wings 21 gives the structured tissue augmentation construct 10 a resting curve such that the tissue-engaging surface 10a is concave along the axis of the central spine 20 and the opposite surface 10b is concave in a similar manner. The flexible lateral wings 21 can extend towards the lateral edges 25a, 25b but do not typically extend out of them such that the terminal ends of the flexible lateral wings 21 are surrounded by the tissue augmentation material 11. In some instances, the central spine 20 can be configured to have the suture limb 12a be passed through it, and in other instances the central spine 20 can include a suture pre-braided along the central spine 20 such that the suture limb 12a extends across the central spine 20 and extends therefrom on one or both opposed ends of the structured tissue augmentation construct 10 (as shown, for examples, in FIGS. 2A-3B). The structured tissue augmentation construct 10 can also be referred to as structured tissue augmentation scaffold or a structured tissue augmentation construct, where construct may also refer to the combination of a tissue augmentation material and a skeleton to form the structured tissue augmentation block/scaffold/construct.

A person skilled in the art will recognize that the dimensions of the length L, width W, and thickness T of the structured tissue augmentation construct 10 can depend on a variety of factors, including but not limited to the size of the filament with which it is to be associated, the anatomy of the patient, and the type of procedure being performed. In some embodiments a ratio of the width W of the structured tissue augmentation construct 10 to a diameter of the suture limb 12a can be approximately in the range of about 2:1 to about 50:1, and more particularly the width W can be at least three times greater than the diameter of the filament or suture with which the structured tissue augmentation construct 10 is associated in some instances. In embodiments in which the suture limb 12a is a suture tape, the width W of the structured tissue augmentation construct 10 can be at least two times greater than the diameter of the suture tape with which the strip is associated in some instances. A person skilled in the art will recognize that the ratio of the width of a structured tissue augmentation block to diameter of the filament or related structure with which the strip is used can be any suitable ratio, depending, at least in part, on the type of filament or related structure being used, the type of strip or other construct being used, and the type of procedure being performed, and thus a ratio of width to diameter may be smaller or larger than those provided for herein. Further, in some embodiments a ratio of the length L of the strip 10 to the width W of the structured tissue augmentation construct 10 can be approximately in the range of about 2:1 to about 20:1, and more particularly the length L can be at least three times greater than the width W in some instances, at least five times greater in some other instances, and at least ten times greater in some instances, although other L-W ratios are possible. Still further, the structured tissue augmentation construct 10 can be substantially flat aside from the curvature imposed by the flexible lateral wings 21 and approximately uniform. In some embodiments a ratio of the width W of the structured tissue augmentation construct 10 to the thickness T of the structured tissue augmentation construct 10 can be approximately in the range of about 2:1 to about 20:1, and more particularly the width W can be at least three times greater than the thickness T in some instances, at least five times greater in some other instances, and at least ten times greater in some instances, although other W-T ratios are possible. A variety of other sizes and shapes of the structured tissue augmentation construct 10, including ratios of the dimensions of the structured tissue augmentation construct 10 and associated components (e.g., the suture limb 12a) can be utilized without departing from the spirit of the present disclosure.

While ratios can be useful to help describe the relationship between the structured tissue augmentation construct 10 and the filament limb 12a, and the relationship between the dimensions of the structured tissue augmentation construct 10, some exemplary, non-limiting dimensions for a tissue augmentation strip can also be useful in understanding the present disclosure. As mentioned above, these dimensions can be dependent on a variety of factors. In some embodiments, the length L can cover a significant portion, to almost an entire portion, of a length of tissue extending between a stitch made in tissue and a bone anchor used to help secure the tissue. In some embodiments, the length L can be approximately in the range of about 5 millimeters to about 4 centimeters, the width W can be approximately in the range of about 5 millimeters to about 20 millimeters, and the thickness T can be approximately in the range of about 0.5 millimeter to about 3 centimeters. Further, while the structured tissue augmentation construct 10 is described as having a length, width, and thickness, and it is shown as being substantially curved about the axis of the central spine 20 in FIGS. 1A-1C, the structured tissue augmentation construct 10 can be relatively flexible and curved in other ways as well, for instance the central spine 20 can be curved such that the structured tissue augmentation construct 10 is curved about an axis that is substantially perpendicular to the central spine 20. Materials used to form the structured tissue augmentation construct 10 are described in a later section of the present disclosure.

A number of techniques can be used to associate the structured tissue augmentation construct 10 with the suture limb 12a, including having the suture limb 12a integrated with the structured tissue augmentation construct 10 (e.g., extending from a continuous length of suture that is pre-braided or integrated with the central spine 20 by being passed through a lumen in the central spine 20). As shown in FIG. 1B, the central spine 20 can extend along all or substantially all of the length L of the structured tissue augmentation construct 10, and the limb 12a can extend from an end of the central spine 20 such that the limb 12a is coupled to the structured tissue augmentation construct 10 by way of being encapsulated with the central spine 20 by the tissue augmentation material 11. The structured tissue augmentation construct 10 can have the suture pre-braided with the central spine 20. In other examples, where the suture limb 12a is associated the central spine 20 before or during a surgical procedure, a process of threading one or more suture limbs 12a through the central spine 20 can be repeated as many times as desired. In some embodiments a suture can be coupled to a thread disposed through the central spine 20 ahead of a procedure so that the operative suture can be threaded through the central spine in vivo during the procedure.

While the structured tissue augmentation construct 10 of FIG. 1B is shown having a primary curve about the axis of the central spine 20, in practice the flexible nature of the central spine 20 and/or the flexible lateral wings 21 can allow the tissue-facing surface 10a to conform to the geometry of the soft tissue that it is contacting. By integrating the structured tissue augmentation construct 10 with the suture limb 12a via the central spine 20, the suture limb 12a can deliver force against soft tissue via a broader foot print (e.g., the tissue-facing surface 10a), thus distributing tension in the suture over more surface area of the tissue. Further, the flexible and curved nature of the lateral wings 21 ensure that the lateral edges 25a, 25b, of the structured tissue augmentation construct 10 make good contact with the tissue as tension in the suture limb 12a across the structured tissue augmentation construct 10 holds the lateral wings 21 in a flexed (e.g., flatter) position, and the wings 21 in turn hold the lateral edges 25a, 25b against the tissue. Further still, the structured tissue augmentation construct 10 may allow force applied to the tissue by the suture limb 12a to be maintained after bioabsorption of the skeleton, as for cases where the skeleton is bioabsorbable, the suture can be braided through the length of the central spine 20 such that, when the central spine 20 is absorbed, the braiding and initial tension of the suture 20 can be maintained without the presence of the central spine 20 while maintaining the association of the suture with the tissue augmentation material 11. Thus, in embodiments where the width of the structured tissue augmentation construct 10 is at least three times greater than the diameter of the suture limb 12a, the force of the suture limb 12a on the tissue may be distributed over an area that is at least three times greater than would otherwise be if no structured tissue augmentation construct 10 was associated with the suture limb 12a. The increased tissue surface area coverage and distributed force of the structured tissue augmentation construct 10 may result in a reduced pressure peak on the soft tissue. Where the soft tissue has become degenerated due to injury or age, a reduction in pressure can result in less chance of abrasion of the tissue. Further, the broader tissue coverage may enhance healing of otherwise compromised tissue.

The suture limb 12a used in conjunction with the tissue augmentation strip 10 can be any type of suture (e.g., braided filament, cannulated filament, mono filament, suture tape, etc.) and can have a size between about a #5 filament (about 20 gauge to about 21 gauge) and about a #3-0 filament (about 29 gauge to about 32 gauge). A person skilled in the art will recognize a variety of other filament types and sizes that can also be used in conjunction with the augmentation strip 10, such as, if a suture tape is used.

Structured Tissue Augmentation Constructs Having Braided Sutures

Aspects of the present disclosure include a tissue augmentation system for tendon repair (such as rotator cuff repair) that includes a flexible or semi-flexible skeleton that is both (i) integrated into a flexible tissue augmentation construct and encapsulated by it and (ii) over-braided by or associated with a suture in order to establish an integrated suture across the length of the tissue augmentation construct. The skeleton can be made from biocompatible (e.g., bioabsorbable) material and includes a central spine with multiple lateral wings extending from it, mostly sideways. FIG. 2A is a top view of the structured tissue augmentation construct 10 of FIGS. 1A-1C, showing an example integration of the central spine with a suture to define a surgical repair system 1. The surgical repair system 1 includes a structured tissue augmentation construct 10, a first suture limb 12a extending from a distal end 29a of the structured tissue augmentation construct 10, and a second suture limb 12b extending from a proximal end 29b of the structured tissue augmentation construct 10. As explained above, the structured tissue augmentation construct 10 includes structural elements, including a central spine 20 extending along substantially all or all of the tissue augmentation material 11 of the structured tissue augmentation construct 10, as well as a first group of flexible lateral ribs 21 extending towards a first lateral side of the tissue augmentation material 11 and a second group of flexible lateral ribs 21 extending towards a second opposite lateral side of the tissue augmentation material 11. The tissue augmentation material 11 can completely surround the central spine 20 and the flexible lateral ribs 21. In some instances, the skeleton is constructed monolithically, such that the central spine 20 and the flexible lateral ribs 21 are a single-piece construction. However, in other examples, the flexible lateral ribs 21 can be separate elements that are connected to the central spine. Additionally, the central spine 20 and/or any of the flexible lateral ribs 21 can be made from one or more individual elements that are coupled together.

Looking at the top view of the surgical repair system 1, the flexible lateral ribs 21 extending laterally from the central spine 20 can have a biased orientation longitudinally (e.g., resembling a fish bone) in the same direction such that the flexible lateral ribs 21 can all be deflected towards the central spine 20 in the same direction. Looking at an end view in FIG. 2B, the flexible lateral ribs 21 can also be oriented towards one side, e.g., a tissue-engaging side, such that in its free or resting state the overall structured tissue augmentation construct 10 is not planar but has a curved or semi-folded geometry as shown in the end view. Therefore, if the tissue-engaging side of the structured tissue augmentation construct 10 is pressed towards a rigid or firm surface by the central spine 20, the flexible lateral ribs 21 will be forced to spring open to maintain full contact between the structured tissue augmentation construct 10 and the surface, as shown in more detail in FIGS. 4A and 4B. Returning to FIGS. 2A and 2B, the structured tissue augmentation construct 10 can be managed and manipulated by first and second suture tails 12a, 12b either attached to ends of the spine or by suture overbraided along the spine, as shown in more detail in FIG. 2C. FIG. 2C shows a detailed top view of the suture 12 braided over the central spine 20 of the structured tissue augmentation construct 10 of FIG. 2A.

Another exemplary embodiment of a structured tissue augmentation construct is shown in a surgical repair system 1' in FIG. 3A. FIG. 3A is a top view of a structured tissue augmentation construct 10' having angled lateral ribs 21'. The structured tissue augmentation construct 10' includes a tissue augmentation material 11 surrounding a central spine 20' that extends from a distal end 29a' of the structured tissue augmentation construct 10' to a proximal end 29b'. The central spine 20' includes a plurality of angled lateral ribs 21', a first group extending towards a first lateral edge and an opposite second group extending towards a second lateral edge. The angled lateral ribs 21' all extend toward the proximal end of the tissue augmentation material 11 at an angle 22' with respect to the central spine 20'. The surgical repair system 1' includes a first suture limb 12a' extending from a distal end of the central spine (which can, in at least some instances, be approximately the distal end 29a' of the structured tissue augmentation construct 10'), a second suture limb 12b' extending from a proximal end of the central spine (which can, in at least some instances, be approximately the proximal end 29b' of the structured tissue augmentation construct 10'), and a length of suture braided on or around the central spine 20' and connecting the first suture limb 12a' with the second suture limb 12b'. FIG. 3B is an end view of the structured tissue augmentation construct 10' of FIG. 3A, and shows that the angled lateral ribs 21' are also angled 23' in the plane that is perpendicular to the central spine 20'.

Yet another exemplary embodiment of a structured tissue augmentation construct 10" is shown in FIG. 3C as an end view. The structured tissue augmentation construct 10" includes a central spine 20" that is at least partially disposed outside of the tissue augmentation material 11" of the structured tissue augmentation construct 10". In this instance, the central spine 20" also illustrates a central lumen 27" that can be used to thread a suture to the structured tissue augmentation construct 10". The structured tissue augmentation construct 10" includes a plurality of angled lateral ribs 21" that extend from the central spine 20" above an opposite non-tissue-engaging surface 10b" and pass towards respective lateral edges 25a", 25b" and into the opposite non-tissue-engaging surface 10b", thereby establishing a concavity of the tissue-engaging surface 10a".

Still another exemplary embodiment of a structured tissue augmentation construct 10''' is shown in FIG. 3D and includes a central spine 20''' that has proximal and distal suture attachments 28a''', 28b''' at distal and proximal ends 29a''', 29b''', respectively, of the structured tissue augmentation construct 10'''. In this structured tissue augmentation construct 10''', the central spine 20''' is not over-braided by a continuous length of suture and is instead configured to have separate lengths of suture attached to the proximal and distal ends 29a''', 29b'''.

Mesh and Lattice Skeletons for Structured Tissue Augmentation Constructs

The structured tissue augmentation constructs can be constructed with flexible or partially skeletons having a variety of different shapes. For example, FIG. 3E shows an exemplary embodiment of a lattice skeleton structure 320 that can be used to construct a structured tissue augmentation construct. The lattice skeleton structure 320 includes a plurality of structural elements arranged to form a latticework or mesh. The lattice skeleton structure 320 has a generally rectangular shape, which can, for example, match the shape of the subsequent structured tissue augmentation construct. The lattice skeleton structure 320 can be integrated with a suture in advance of being used to construct the tissue augmentation construct. As shown in FIG. 3E, the lattice skeleton structure 320 has a distal end knot 328a securing a length of suture 312 to the distal end of the lattice skeleton structure 320, as well as a proximal end knot 328b securing a different point of the suture 312 to the proximal end of the lattice skeleton structure 320 such that the suture 312 spans a length of the lattice skeleton structure 320 between the knots 328a, 328b and forms both a distal tail 312a and a proximal tail 312b. FIG. 3F is an end view of the lattice skeleton structure 320, showing that the lattice skeleton structure 320 has a curved shape about its longitudinal axis (e.g., into the page), which will ultimately form a tissue-engaging surface of a structured tissue augmentation construct above the convex side of the lattice skeleton structure 320, as shown in FIG. 3H.

FIG. 3G shows a structured tissue augmentation construct 310 constructed with the lattice skeleton structure 320 of FIG. 3E. In FIG. 3G, and as also shown in FIG. 3G, the material of the structured tissue augmentation construct 310 can completely encapsulate the lattice skeleton structure 320, with the distal and proximal suture tails 312a, 312b extending from proximal and distal ends of the structured tissue augmentation construct 310.

Methods of Use—Repairing Soft Tissue

In operation, the structured tissue augmentation constructs 10, 10', 10'', 10''' described herein all include a convex tissue-engaging surface that is configured to flex or splay outwards against a soft tissue surface when the suture limbs at the ends of the structured tissue augmentation construct are tightened to force the structured tissue augmentation construct against the tissue. FIGS. 4A and 4B are end views the structured tissue augmentation construct 10' of FIG. 3A being disposed against soft tissue during a surgical procedure. The tissue-engaging surface 10a' is disposed against a soft tissue 30 in advance of the suture limbs 12a', 12b' being tightened to apply a load 99 against the central spine 20' that urges the central spine 20' towards the soft tissue, as shown in FIG. 4B. With the load 99 applied to the central spine 20', the tissue-engaging surface 10a' is urged towards the soft tissue 30 against the spring restoration force of the flexible angled lateral ribs 20' until all or substantially all of the tissue-engaging surface 10a' is pressed against the soft tissue 30. The flexible nature of the angled lateral ribs 21' distributes the force applied to the central spine 20' by the suture limbs 12a', 12b' to the lateral edges of the structured tissue augmentation construct 10', thereby ensuring the contact of the tissue-engaging surface 10a' against the soft tissue. The structured tissue augmentation construct 10' includes a force at the lateral edges, as well as under the central spine 20', if the load 99 is sufficient to urge the tissue-engaging surface 10a' under the central spine 20' against the soft tissue 30. Additionally, due to the resting angle of the flexible angled lateral ribs 21', the resting width d1 of the structured tissue augmentation construct 10' is less than the splayed width d1'. The structured tissue augmentation construct 10' can have a resting or expanded configuration (expanded because the angled lateral ribs 21' hold the ends of the construct 10' apart), as shown in FIB. 4A, as a result of the biasing provided by the angled lateral ribs 21'. Accordingly, the structured tissue augmentation construct 10' can have different compressed configurations, depending on how the angled lateral ribs 21' are deflected. In FIG. 4B, with the angled lateral ribs 21' splayed by the soft tissue, the structured tissue augmentation construct 10' can be said to have a compressed configuration or an installed configuration. As is shown in FIG. 5A, the structured tissue augmentation construct 10' can also have a constricted configuration when the angled lateral ribs 21' are deflected towards the central spine 20' such that the width of the structured tissue augmentation construct 10' is reduced (e.g., to enables the structured tissue augmentation construct 10' is be disposed in a delivery tube). In operation, the biasing nature of the angled lateral ribs 21' serves the urge the structured tissue augmentation construct 10' into the expanded or resting configuration absent an external forces.

Figure 5B:
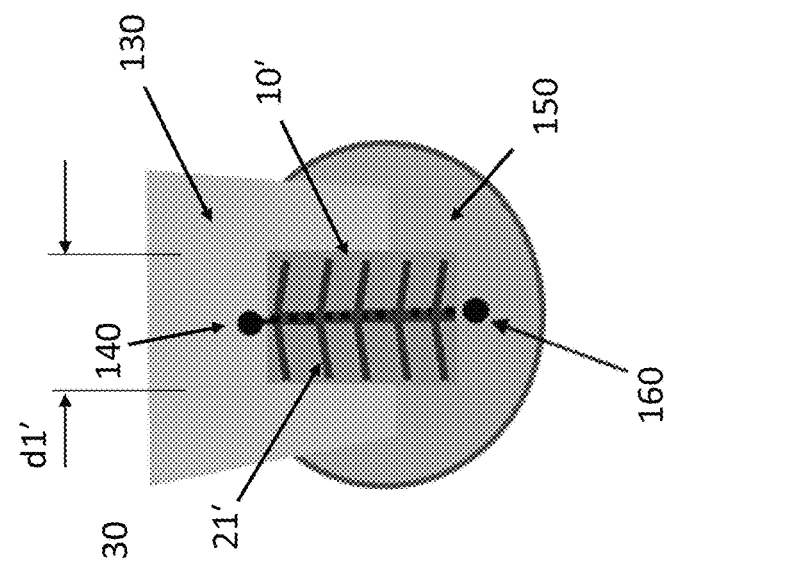
FIGS. 5B-5D are schematic sequential views of one exemplary embodiment for installing a structured tissue augmentation construct in a single row fixation.
Figure 5C:
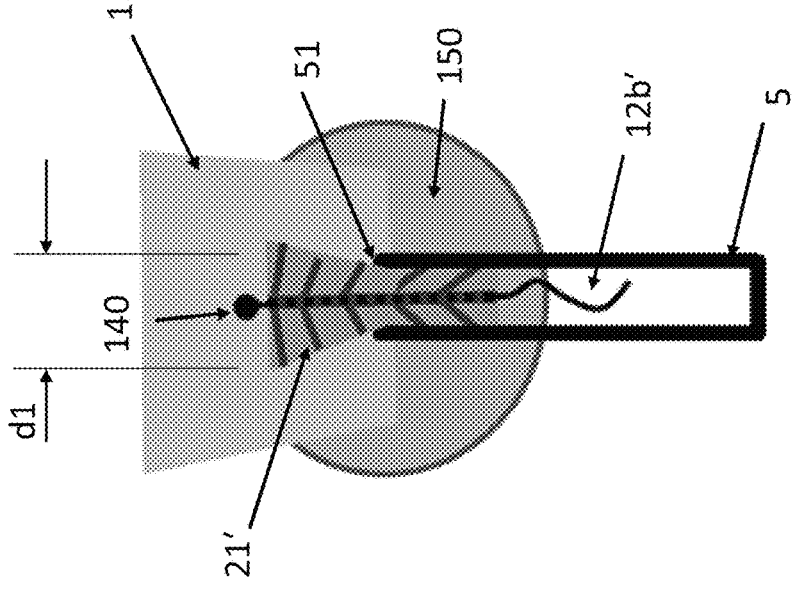
Figure 5D:
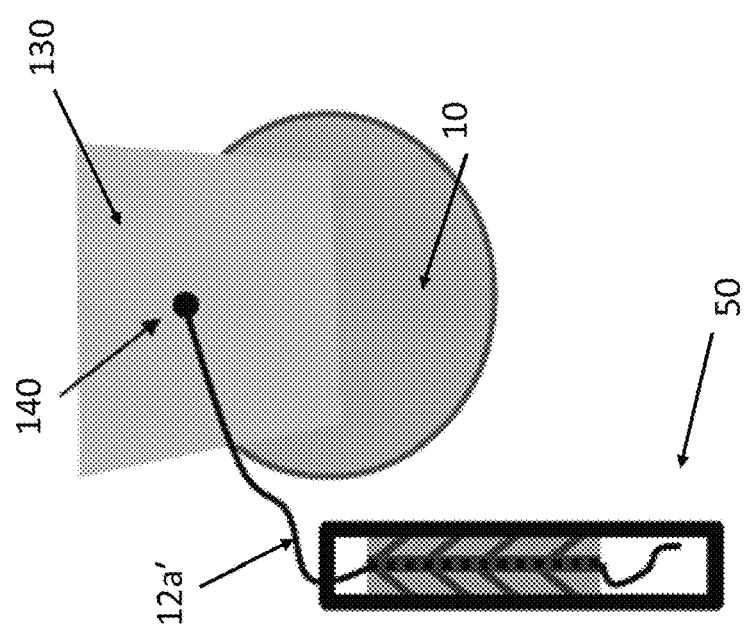

In an example surgical repair operation, the structured tissue augmentation construct 10' can begin disposed in a delivery tube 50 in a collapsed state as shown in FIG. 5A. Together, the construct 10', suture limbs 12a', 12b', and delivery tube 50, in combination with other constructs (and/or constructs more generally), limbs, and/or tubes (and/or other delivery devices), can form portions, or all, of a surgical kit 5. The ability of the structured tissue augmentation construct 10' to be collapsible such that the structured tissue augmentation construct 10' can be constricted into a delivery tube 50 to a smaller diameter d0 (as compared with the resting diameter d1' of FIG. 4A) and then, upon removal from the delivery tube 50, expand back to a resting state is enabled by the flexibility of the angled lateral ribs 21'. The angled lateral ribs 21' compress in the same direction against the central spine 20', as shown in FIG. 5A, and then expand outward from the central spine 20' to return the structured tissue augmentation construct 10' to the resting configuration shown in FIG. 3A. Returning to FIG. 5A, with the structured tissue augmentation construct 10' disposed in the delivery tube, first and second suture limbs 12a', 12b' can extend from the ends 51 of the delivery tube 50 to allow securing of the suture limbs 12a', 12b' before removal of the construct 10'. For example, as shown in FIG. 5B, with the distal suture limb 12a' being secured to a medial fixation 140 in soft tissue before the construct 10' is removed from the delivery tube 50. FIGS. 5B-5D are schematic sequential views of one exemplary embodiment for installing a construct 10' in a single row fixation and delivering the construct 10' into the operative environment via a delivery tube 50. During delivery and fixation, the distal suture limb 12a' is first passed through a medial location in the soft tissue 130 to tie the distal end of the skeleton of the construct 10' at that point. The delivery tube 50 can then be retracted, as shown in FIG. 5C, allowing the collapsed angled lateral ribs 21' to spring open spreading the construct 10' laterally back to its resting state. The proximal suture limb 12b' is then fixated to the bone 160, and further tightening of either or both suture limbs 12a', 12b' urges the tissue-engaging surface of the construct 10' against the soft tissue 130 to spring-load the construct 10' against the soft tissue 130.

Materials for Forming Structured Augmentation Constructs

The structured constructs discussed above, e.g., the constructs 10, 10', as well as those provided for further below can be made of one or more biocompatible, bioresorbable materials so that after implantation into a patient to replace or repair connective tissue, the strip gradually degrades or remodels over time. The resorption profile of the constructs can be sufficiently long to reinforce and provide structure to tissue during the regeneration or healing process. A person skilled in the art can determine a suitable resorption profile, depending, at least in part, on the desired use of the construct, and can tailor the resorption profile by varying the materials used to form the structured construct.

While many different materials can be used to form the structured tissue augmentation constructs, either alone or in combination with other materials, in some instances the material is a biocompatible polymer. Exemplary embodiments of suitable biocompatible materials synthetic polymers, natural polymers, and combinations of the two. As used herein, the term "synthetic polymer" refers to polymers that are not found in nature, even if the polymers are made from naturally occurring biomaterials. As used herein, the term "natural polymer" refers to polymers that are naturally occurring. In embodiments where the structured tissue augmentation constructs includes at least one synthetic polymer, suitable biocompatible synthetic polymers can include polymers selected from the group that includes: aliphatic polyesters, poly(amino acids), copoly(ether-esters), polyalkylene oxalates, polyamides, tyrosine derived polycarbonates, poly (iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), poly(propylene fumarate), poly(hydroxyalkanoate), polydioxanone, poly-hydroxybutyrate-co-hydroxyvalerate, polyamniocarbonate, polytrimethylene, polyoxaamides, elastomeric copolymers, and/or combinations or blends thereof. Suitable synthetic polymers for use in the structured tissue augmentation constructs can also include biosynthetic polymers based on sequences found in: collagen, a collagen scaffold, pulverized collagen pieces, elastin, thrombin, silk, keratin, fibronectin, starches, poly(amino acid), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides, and/or combinations or blends thereof. The types of materials that can be used to construct structured tissue augmentation constructs, either wholly or in part, include non-absorbable polymers selected from the group that includes: polyethylene, polypropylene, polyetheretherketone (PEEK), polyethylene terephthalate (PET), polytetrafluoroethylene, silicone, rubber, or other biocompatible non-absorbable polymers, and/or combinations or blends thereof. Natural polymers for the use in structured tissue augmentation construct 10 can be selected from the group that includes: a fibrin-based material, collagen-based material, a hyaluronic acid-based material, a cellulose-based material, a silk-based material, a gelatin-based material, a glycoprotein-based material, a cellulose-based material, a polysaccharide-based material, a protein-based material, a fibronectin-based material, a chitin-based material, a pectin-based material, an elastin-based material, an alginate based material, a dextran-based material, an albumin-based material, a natural poly(amino acids) based material, a decellularized tissue, purified extracellular matrix (ECM), a demineralized bone matrix, and/or combinations or blends thereof.

Still further, virtually any type of tissue can be used to form the structured tissue augmentation constructs, including but not limited to: autograft tissue and allograft tissue, as well as human allogeneic tissue and xenogeneic tissue, which includes porcine, bovine, and/or equine, among others. The tissue used can be selected from biological connective tissues that include: ligament tissue, tendon tissue, a modeled tendon, skin tissue, muscle tissue, periosteal tissue, pericardial tissue, synovial tissue, dermal tissue, an acellular porcine dermal matrix, an acellular bovine dermal matrix, fascia, small intestine tissue, embryonic tissue, amniotic tissue, placental tissue, periodontal tissue, peritoneum tissue, vascular tissue, blood, and/or combinations or blends thereof. The materials used to form the structured tissue augmentation constructs can be cross-linked and non-cross-linked, and any material provided for herein can be used in conjunction with other materials, whether synthetic, natural, and/or a combination or blend thereof. Still further, the structured tissue augmentation constructs, and/or materials used to form the structured tissue augmentation constructs, can be treated with platelet-rich plasma (PRP), bone marrow, cells, and/or other bone and/or tissue growth-promoting materials.

The material used to form the structured tissue augmentation constructs can be made and/or formed, using a variety of techniques. These techniques include, but are not limited to, knitting them, braiding them, and/or weaving them. The overall construction of the materials can be described as being woven, knitted, non-woven, and/or a foam, among other constructions resulting from techniques known to a person skilled in the art. Further, a combination of techniques can be used for a single construct, and/or a portion(s) thereof. The formation techniques can be used with materials, e.g., synthetic polymers and other materials provided for above, as well as tissue.

In some embodiments, the structured tissue augmentation construct can be prepared such that a basement membrane is not included. A basement membrane is the thin, fibrous tissue separating the epithelium from the underlying tissue located between the epidermis and connects, and functionally separates, the epidermis and the dermis. While a basement membrane can add strength to a structured tissue augmentation construct, such as a dermis construct, the inclusion of such a membrane makes the membrane "oriented" such that only one side, the epithelial side, should be the side that is placed in contact with tissue. Otherwise, dermis patch integration to the host tissue will be, at the very least, significantly slower. It can be difficult for a surgeon, during the course of a procedure, to easily identify which side is the epithelial layer.

As an improved alternative, the present disclosure contemplates taking actions to remove the basement membrane from the structured tissue augmentation construct. This can be done by, for example, cutting off or splitting the basement membrane from the rest of a structured tissue augmentation construct. Alternatively, or additionally, a material conductive to dermis patch integration can be associated with a side of the construct that includes (or once included) the basement membrane.

Tissue Augmentation Kits

The filaments and structured tissue augmentation constructs provided for herein can be included together as part of a soft tissue repair kit. Such a kit can also include components such as a delivery tube, installation tool, bone anchors, and/or a bone drill. For example, one exemplary embodiment of a kit can include one or more structured tissue augmentation constructs and one or more delivery tubes. In some instances, the structured tissue augmentation constructs can be pre-disposed on the sutures. The structured tissue augmentation constructs can include any of the constructs provided for herein or otherwise derivable from the present disclosures, including but not limited to the tissue augmentation constructs 10, 10', 10", and/or variations thereof derivable by a person skilled in the art in view of the present disclosures. In some instances, structured tissue augmentation constructs are pre-disposed in the delivery tube 50.

The kit can also include other components used in conjunction with structured tissue augmentation constructs and delivery tubes, including but not limited to one or more sutures, such as the sutures 12, 12a, 12b, 12a', 12b', one or more installation tools, such as the delivery tube 50, one or more implants, e.g., bone anchors, and one or more bone drills. In some exemplary embodiments the kit can include a tissue augmentation construct 10, 10', 10" and a suture 12 that will be anchored over the soft tissue. The types and configurations of the filaments, constructs, installation tools, and bone anchors can be varied, thus providing the user options for use in any surgical procedure. Accordingly, any combination of constructs having a strip or tape configuration (e.g., construct 10 or construct 10') can be mixed and matched by a surgeon, as desired. The selection of constructs to be used can depend, at least in part, on a variety of factors, including but not limited to the anatomy of the patient and the type of procedure being performed.

The delivery tube 50 and/or installation tool can be a single device used to associate structured tissue augmentation constructs to limbs multiple times, or multiple delivery tubes and tools can be provided to allow multiple strip-limb combinations to be formed or to allow for different configurations preferred by different users. The delivery tube and/or installation tool can be specifically adapted to be used with particular structured tissue augmentation constructs, procedures, and/or surgeon's preferences without departing from the spirit of the present disclosure.

To the extent implants such as anchors are provided as part of a kit, or used in conjunction with any of the disclosures provided for herein, the implants can be any type of implant known to those skilled in the art that are used for various types of tissue repair procedures. For bone anchors, the anchors can be of a hard construction or a soft construction, and in some instances they can be knotless anchors, meaning filaments associated therewith do not need to have knots tied by the surgeon during the surgical procedure to couple the tissue to the filament and/or the anchor. Some exemplary embodiments of hard suture anchors for use in the kits or more generally with the present disclosures include Healix Ti™ anchors that are commercially available from DePuy Synthes, as well as Healix Advance™ anchors, Helix Advance Knotless™ anchors, Healix BR™ anchors, Healix PEEK™ anchors, Healix Transtend™ anchors, Bioknotless® anchors, Gryphon® anchors, Fastin® anchors, Versalok® anchors, Microfix® anchors, Minilok™ anchors, MicroQuickanchors® anchors, and/or Tacit® anchors, each of which is also commercially available from DePuy Mitek, Inc. Some exemplary embodiments of soft suture anchors for use in the kits or more generally with the present disclosures include those described in U.S. Pat. No. 9,345,567 of Sengun, the content of which is incorporated by reference herein in its entirety.

To the extent the kit includes a bone drill, any type of bone drill known by those having skill in the art for forming bone holes in which anchors can be disposed can be provided.

Methods of Use—Rotator Cuff Repairs

Exemplary methods for using systems, devices, and kits of the type described herein are now described in greater detail. While the methods described herein generally relate to attaching soft tissue to bone, and in this section of the disclosure are primarily discussed with respect to rotator cuff repairs, a person skilled in the art will recognize other types of procedures and repairs with which the constructs and the methods related to the same can be used. Further, to the extent a particular type of structured tissue augmentation construct is illustrated in the following embodiments, a person skilled in the art would understand how to employ other structured tissue augmentation constructs provided for herein without departing from the spirit of the present disclosures. Likewise, any sutures or anchors provided for herein or otherwise known to those having skill in the art can be used, including knotless anchors. Still further, while in the illustrated embodiments the lengths of sutures and limbs may be approximately equal, any suture or limb can be any desired length, and thus lengths of sutures and limbs do not need to be equal. Likewise, to the extent the techniques described below discuss having a certain number of suture limbs (e.g., one, two, three, etc.) extending from or otherwise associated with a suture anchor to perform the tissue repair, a person skilled in the art, in view of the present disclosures, will understand how a different number of limbs can be used to perform the same, or a similar type, of repair.

Rotator Cuff Repairs—Double Row Applications

Figure 6A:
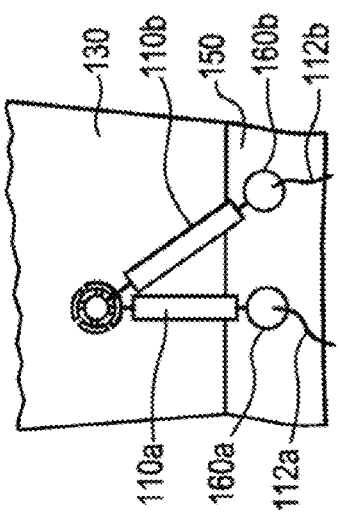
FIGS. 6A-6C are schematic sequential views of one exemplary embodiment for installing two structured tissue augmentation constructs in a double row fixation.
Figure 6B:
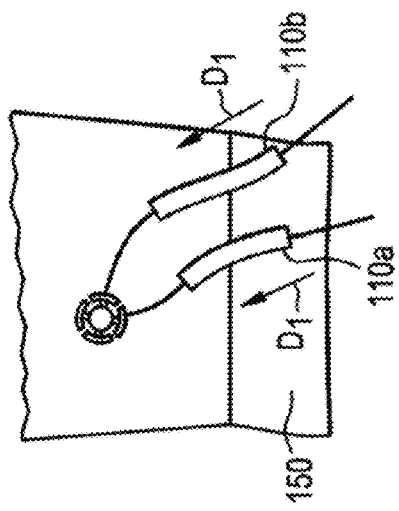
Figure 6C:
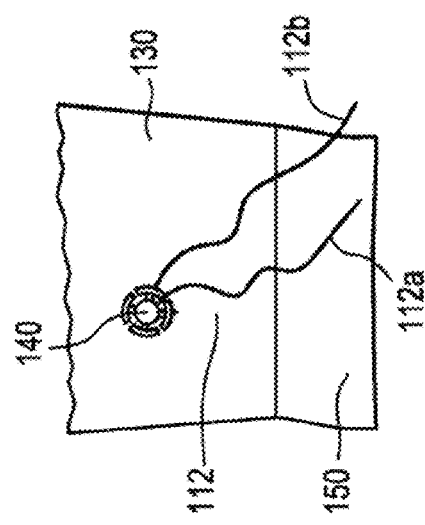

A first exemplary method of soft tissue repair using two separate structured tissue augmentation constructs 110, illustrated as constructs 110a, 110b, in conjunction with a double row application or repair is shown in FIGS. 6A-6C. The method involves fixing a piece of soft tissue 130, e.g., rotator cuff, with respect to bone 150. If the structured tissue augmentation constructs 110a, 110b are delivered in a delivery tube, the structured tissue augmentation constructs 110a, 110b can be removed from the delivery tubes before or during the procedure. An incision can be made to perform the procedure using any one of a traditional open repair, an arthroscopic repair, or a mini-open repair. Once the surgeon has access to the surgical site and the tissue and bone have been prepared according to accepted surgical techniques, the surgeon can use a fixation 140 (e.g., a medial row stitch of a same or separate suture) to secure the suture 112 in the soft tissue 130 of two different structured tissue augmentation constructs. Alternatively, any known stitch can be used. As shown in FIGS. 6A-6C, the medial row stitch 140 has two suture limbs 112a, 112b extending outwardly from the soft tissue, each having an associated structured tissue augmentation construct.

As shown in FIG. 6B, the structured tissue augmentation constructs 110a, 110b have the separate suture limbs 112a, 112b, respectively. In other instances, a single suture 112 can be used with a subsequent step of threading structured tissue augmentation 110a, 110b onto the suture limbs 112a, 112b by hand, if the structured tissue augmentation constructs 110a, 110b are not already integrated with the limbs 112a, 112b.

Once the suture limbs 112a, 112b of the structured tissue augmentation constructs 110a, 110b have been associated with the medial row switch 140 (or other fixation), the structured tissue augmentation constructs 110a, 110b can be advanced in the direction $D_1$ by shortening the respective suture limbs 112a, 112b with respect to the fixation 140. In the illustrated embodiment, the constructs 110a. 110b are disposed proximate to the fixation 140 because the length of the constructs 110a, 110b is similar to the length of the distance extending between the medial stitch 140 and the end of the tissue 130. However, in embodiments in which the length of the constructs 110a, 110b is less than that distance, the constructs 110a, 110b may not necessarily be proximate to the medial stitch 140, but can extend along some portion of the length of the limbs 112a, 112b extending between the medial stitch 140 and the end of the tissue 130. After the constructs 110a, 110b have been installed on the respective suture limbs 112a, 112b, the free ends of the suture limb 112a, 112b can be secured within the body. For example, the free ends of each suture limb 112a, 112b can be coupled to respective anchors 160a, 160b and the fixation 140, as shown in FIG. 6C, which in some exemplary embodiments can be knotless anchors. The suture limbs 112a, 112b can then be tightened to secure the soft tissue 130 to the bone 150 before the anchors 160a, 160b are fully fixed in the bone 150, thus completing the double row lateral fixation associated with the fixation 140.

This procedure can be repeated as many times as required to satisfactorily fixate the soft tissue 130 to the bone 150. While the patient is healing from the procedure, new bands of tendon like tissue can form around the suture limbs 112a, 112b and into and around the constructs 110a, 110b to result in a more robust tissue formation in the soft tissue and between the soft tissue and bone. For example, constructs made from collagen scaffold or acellular dermal matrix material can be capable of remodeling while the patient is healing from the procedure into tendon like tissue and integrate with the native tissue. The additional coverage of tendon like tissue across the soft tissue can increase the strength of the tissue-to-bone connection and may prevent further injury. Additionally, if the flexible skeleton of the structured tissue augmentation constructs is bioabsorbable, it can be absorbed by the patient during the healing process.

Rotator Cuff Repairs—Single Row Applications

Another method of soft tissue repair is illustrated in FIGS. 7A-7C. The method fixates soft tissue 130' to bone 150' using a single row application. Once the surgeon has access to the surgical site and the tissue, bone, and structured tissue augmentation constructs 110a', 110b' have been prepared according to accepted surgical techniques, including those provided for herein, the surgeon can use an initial mattress stitch or fixation to install suture 112' in the soft tissue 130'. Alternatively, any known stitch can be used. The fixation 140' can be used to couple two suture limbs 112a', 112b' of two corresponding structured tissue augmentation constructs 110a', 110b' extending outwardly from the soft tissue.

As shown in FIG. 7B, the structured tissue augmentation constructs 110a', 110b', each having a suture limb 112a', 112b', respectively, are advanced in the direction $D_1$ by tightening the suture limbs 112a', 112b' until they are proximate the mattress stitch 140'. As described above, the location of the strips with respect to the stitch 140' can depend, at least in part, on the size of the constructs 110a', 110b' and the distance between the stitch 140' and the end of the tissue 130'. After the constructs 110a', 110b' have been installed on the respective suture limbs 112a', 112b', the free ends of the suture limbs 112a', 112b' can be secured within the body, for instance, by attaching them to a single anchor 160' and fixation 140', as shown in FIG. 7C. The suture limbs 112a', 112b' can be tightened to secure the soft tissue 130' to the bone 150' before the anchor 160' is fully fixed in the bone 150', thus completing the single row fixation associated with the medial stitch 140'.

Figure 8C:
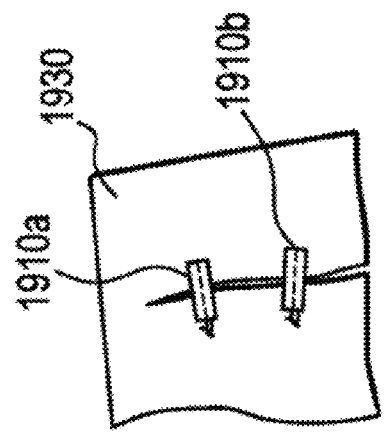
FIGS. 8A-8C are schematic sequential views of another exemplary embodiment for repairing soft tissue.
Figure 8B:
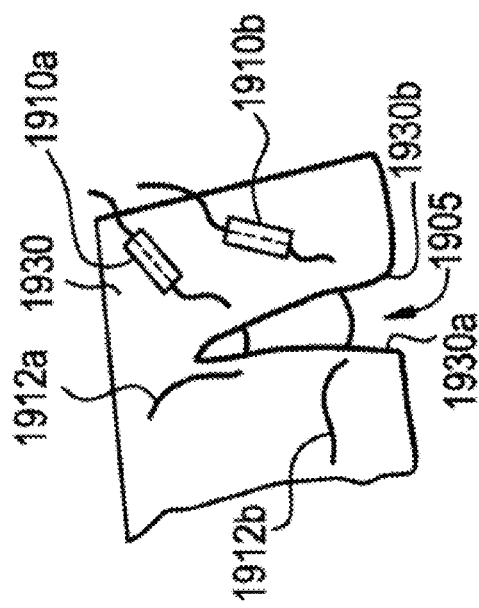
Figure 8A:
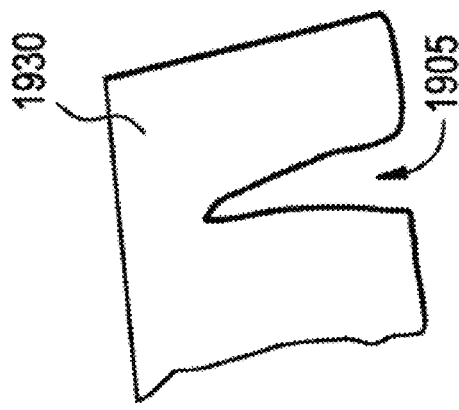
Figure 8D:
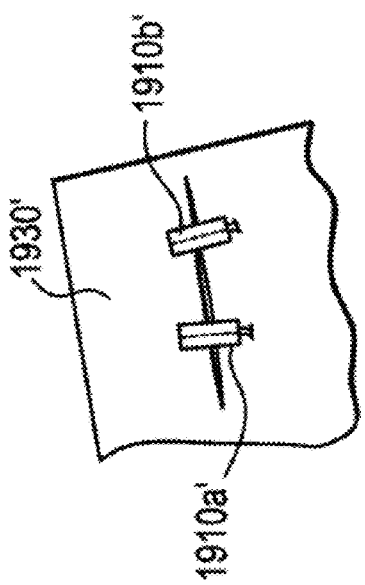
FIGS. 8D-8F are schematic sequential views of yet another exemplary embodiment for repairing soft tissue.
Figure 8E:
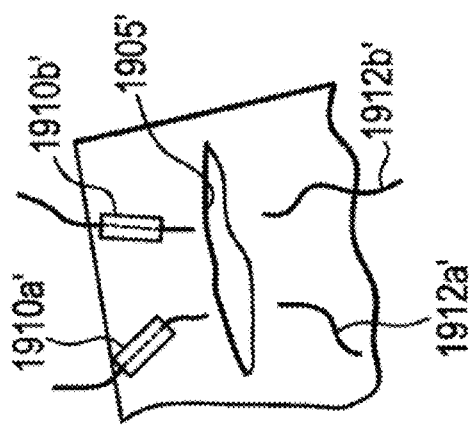
Figure 8F:
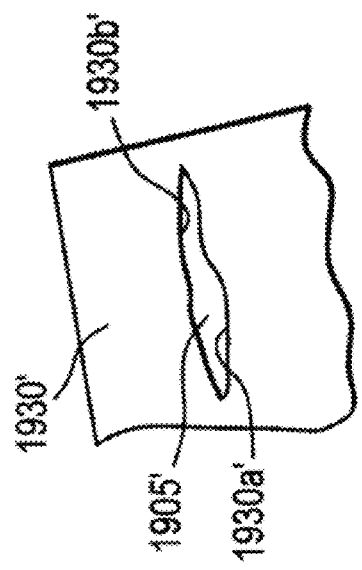

Repairing Soft Tissue by Closing Gaps—Rotator Cuff and Non-Rotator Cuff Examples Two exemplary embodiments for closing gaps or voids in tissue are illustrated in FIGS. 8A-F. The first illustrated embodiment, as shown in FIGS. 8A-8C, relates to a rotator cuff margin convergence, and the second, as shown in FIGS. 8D-8F, a hip capsular closure. However, a person skilled in the art will recognize other types of procedures these embodiments can be applied to in practice without departing from the spirit of the present disclosure.

FIG. 8A shows rotator cuff tissue 1930 having a void or gap 1905. First and second sutures 1912a, 1912b can be associated with first and second constructs 1910a, 1910b using techniques provided for throughout the present disclosure. As shown in FIG. 8B, a first free end of the first suture 1912b can be threaded into the rotator cuff tissue 1930 on a first side of the void 1905 and threaded back through the rotator cuff tissue 1930 on the opposite side of the void 1905. The first free end can be tied to the second free end to bring edges 1930a, 1930b of the void 1905 together. This process can be repeated for the second suture 1912b to complete the repair, as shown in FIG. 8C. The structured tissue augmentation constructs 1912a, 1912b can provide the many benefits provided for herein, including but not limited to increased surface area through which forces from the sutures 1912a, 1912a can be distributed, protection of a knot used to couple free ends of the sutures 1912a, 1912b, and providing a scaffold for new tissue to grow to create a stronger repair between the edges 1930a and 1930b, with the scaffold essentially becoming a new layer of tissue on top of the existing rotator cuff tissue 1930.

FIG. 8D shows hip capsular tissue 1930' having a void or gap 1905'. First and second sutures 1912a', 1912b' of first and second structured constructs 1910a', 1910b' are used according to techniques provided throughout the present disclosure. As shown in FIG. 8E, a first free end of the first suture 1912a' can be threaded into the hip capsular tissue 1930' on a first side of the void 1905' and threaded back through the hip capsular tissue 1930' on the opposite side of the void 1905'. The first free end can be tied to the second free end to bring edges 1930a', 1930b' of the void 1905' together. This process can be repeated for the second suture 1912b' to complete the repair, as shown in FIG. 8F. As with the structured tissue augmentation constructs 1912a, 1912b, the structured tissue augmentation constructs 1912a', 1912b' can provide the many benefits provided for herein, including the highlighted benefits provided for with respect to the structured constructs 1912a, 1912b.

Augmenting Soft Tissue Repair with Structured Tissue Augmentation Constructs

Example methods of the present disclosure also include using structured tissue augmentation constructs to supplement existing tissue repair methods and techniques. For examples, FIGS. 9A-9E shows sequential views of an exemplary embodiment for repairing soft tissue using a structured tissue augmentation construct to augment a single row fixation. The construct provided for in the present disclosures can help expand the coverage area of a tissue augmentation construct in conjunction with various soft tissue repairs, for example starting from a medial cuff over to a lateral bone lengthwise approximately in the range of about 10 millimeters to about 15 millimeters widthwise.

Figure 9C:
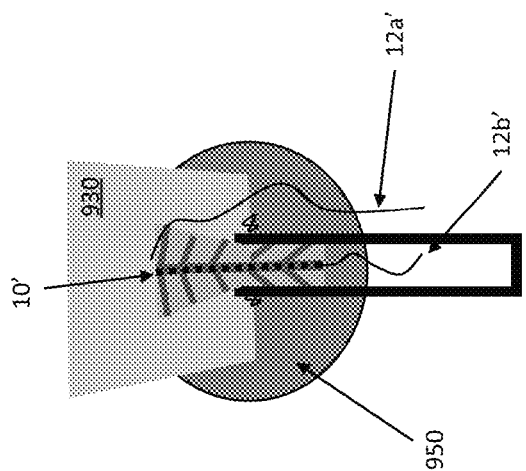
FIGS. 9A-9E are schematic sequential views of still another exemplary embodiment for repairing soft tissue.
Figure 9B:
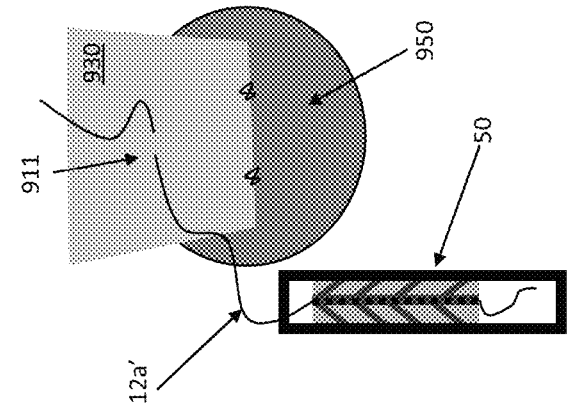
Figure 9A:
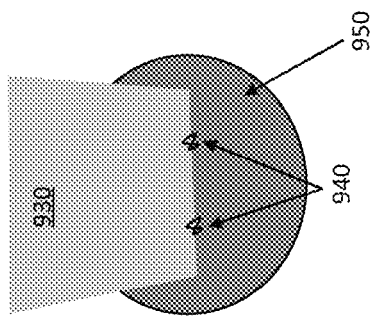
Figure 9D:
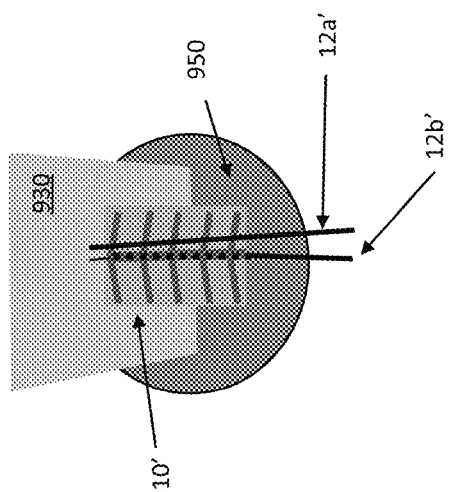
Figure 9E:
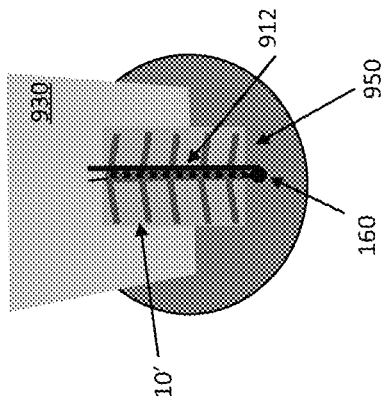

FIG. 9A shows a tendon 930 repaired using two single row fixations 940 to a bone 950. In FIG. 9B, the delivery tube 50 is used to introduce the structured tissue augmentation construct 10' and the distal suture limb 12a' of the construct 10' is coupled with the medial part of tendon 930 using a mattress pass 911. In FIG. 9C, the distal suture limb 12a' is tensioned to draw the construct 10' out of the delivery tube 50 and, once removed, as shown in FIG. 9D, the construct 10' is expanded by the resiliency of the internal skeleton 20' and positioned with its tissue-engaging surface above the tendon 930, the two single row fixations 940, and the bone 950. Once positioned, the distal suture limb 12a' can be crossed over the spine 21' of the construct 10' and can be affixed, together with the proximal suture limb 12b' to an anchor 160, as shown in FIG. 9E. The suture limbs 12a' and 12b' spanning from the medial tendon to lateral anchor 160 provide addition security to the single row fixations.

Methods of Manufacturing Structured Tissue Augmentation Constructs—General Methods Structured tissue augmentation constructs can be manufactured and/or assembled in a variety of different ways. For example, a skeleton can be placed between two layers of tissue augmentation material. The two layers of tissue augmentation material can be attached to each other using a variety of techniques, including but not limited to being glued, sutured, and/or stapled together. Another example includes placing an appropriate polymer solution into a mold set-up that includes the skeleton. Thereafter, the mold set-up can be cooled and/or lyophilized. In still other examples of manufacturing a construct having a skeleton as provided for herein, a polymeric solution can be formed around a skeleton using techniques such as electrospinning, forcespinning, meltspinning, pneumatospinning, extrusion, and/or combinations of those techniques, or other similar techniques that achieve the same desired outcome. In some instances, polymeric fiber(s) can be braided around the skeleton. By way of still a further example, a skeleton can be pressed into a sheet made of one or more of the tissue augmentation materials described herein.

The embodiments described above represent some specific techniques associated with manufacturing structured tissue constructs having particular configurations, e.g., strips, bars, and patches. Such techniques can be adapted by a person skilled in the art for use in other configurations of structured tissue augmentation constructs in view of the present disclosures. Still further, the present disclosure provides for even more general techniques and methods that can be used to form the various structured tissue augmentation constructs disclosed herein derivable from the present disclosures. The methods provided for in this section can be used as standalone methods, in conjunction with each other, and/or in conjunction with the other manufacturing techniques provided for in the present disclosure.

In some embodiments, the constructs can be fully, or partially, manufactured by phase separation techniques, lyophilization, knitting, weaving, electrospinning, forcespinning, meltspinning, pneumatospinning, extrusion, rapid prototyping (e.g., 3-D printing), and/or combinations of those techniques, or other similar techniques that achieve the same desired outcome. In order to facilitate tissue in growth, perforations can be created in the construct using thermal, electrical, or/and mechanical means, among others. For example, the perforations can be created by a laser or a sharp object such as a needle, punch, or die. The size of a perforation can be any suitable size, but preferably, the perforations are sized to allow tissue in-growth. More preferably, the perforations size can be approximately in the range of about 50 microns to about 2000 microns, and even more preferably, approximately in the range of about 50 microns to about 1000 microns.

In some embodiments, a biological tissue including, but not limited to, an allograft or xenograft tissue, may, optionally, be incorporated within the various structured tissue augmentation constructs, thus forming a two-layer construct. The combination of a biological tissue within the various structured tissue augmentation constructs can provide for enhanced biological performance and mechanical performance of a resulting construct.

For example, a structured construct can include a reconstituted collagen matrix or a biodegradable polymer, or any of the other materials described herein for use in a structured tissue augmentation construct (e.g., autograft, xenograft, pulverized collagen pieces, porcine dermis, etc.), and a biological component, such as an extracellular matrix (ECM), attached to one side of the matrix using techniques known to those skilled in the art. The reconstituted collagen matrix or biodegradable polymer can be, or can be part of, a first layer, and the biological component can be, or can be part of, a second layer, with a thickness and a surface area of the first layer being larger, and as shown substantially larger, than a thickness and a surface area of the second layer. In other embodiments, the biological component, e.g., the ECM, can be disposed on opposed sides of the matrix and/or coated or soaked onto the matrix. A person skilled in the art will recognize a number of different attachment options that can be used to couple the ECM(s) to the matrix, including but not limited to gluing and stitching. The inclusion of the ECM or other biological component can help integrate the augmentation construct with the tissue with which the construct is being used. In one exemplary embodiment, the matrix can have a thickness $T_1$ approximately in the range of about 1 millimeter to about 4 millimeters, and the ECM layer can have a thickness approximately in the range of about 80 microns to about 3 millimeters.

In some embodiments, a biological component can be coated onto the structured tissue augmentation construct, or incorporated in the structured tissue augmentation construct. If a biological component is coated onto the structured tissue augmentation construct, the biological component is preferably associated with at least a portion of the construct. For example, the biocompatible construct can include an adhesion agent for anchoring the suspension of the biological component to a scaffold. The adhesion agent can be an anchoring agent, a cross-linking agent (i.e., chemical or physical), and combinations thereof. Suitable anchoring agents can include, for example, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, Matrigel, Monostearoyl Glycerol co-Succinate (MGSA), Monostearoyl Glycerol co- Succinate/polyethylene glycol (MGSA/PEG) copolymers, laminin, elastin, proteoglycans, and combinations thereof.

Cross-linking can be achieved using physical means and chemical agents. Examples of chemical agents used to cross-link can include dehydrothermal (DHT) treatment, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hexamethylene diisocyanate, 1-Ethyl-3-[3-dimethylaminopropyl]carbodiimide hydrochloride (EDC or EDAC), hydroxychloride, N-hydroxysuccinimide, light (e.g., blue light and UV light), pH, temperature, and combinations thereof.

The biological components can be one or more effectors that promote healing and/or regeneration of the affected tissue at the site of injury. The biological component of a construct can include heterologous or autologous growth factors, proteins, matrix proteins, peptides, antibodies, antibiotics, anti-inflammatories, therapeutic agents, chemotactic agents, antimicrobial agents, antibiotics, anti-inflammatory agents, compounds that minimize or prevent adhesion formation, compounds or agents that suppress the immune system, cell attachment mediators, biologically active ligands, integrin binding sequence, enzymes, cytokines, glycosaminoglycans, polysaccharides, viruses, virus particles, nucleic acids, analgesics, cells, platelets, platelet rich plasma (PRP), minced extracellular particles, minced tissue fragments, hydroxyapatite, tricalcium phosphate, bioactive glass, biphasic calcium phosphate, calcium sulfate, other bone and/or tissue growth-promoting materials, and/or combinations thereof.

In some embodiments, the construct can be made of more than one layer. The layers of the construct can be made of the same material or different materials and the skeleton can be disposed between two or more of the layers. The layers can be bonded or fused together using sutures, mechanical, electrical, and chemical fastening techniques. Examples of bonding or fusing can include, for example, tissue welding, staples, rivets, tissue tacks, darts, screws, pins, arrows, cross-linking, vacuum pressing, compression, compression combined with dehydration, vacuum pressing combined with dehydration, or a biological adhesive or a combination thereof. Dehydration in this context can include, for example, freeze-drying (i.e., lyophilization). Biological adhesives can include, for example, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly (amino acid)-based adhesive, cellulose-based adhesive, polysaccharide-based adhesive, synthetic acrylate-based adhesives, platelet rich plasma (PRP), platelet poor plasma (PPP), clot of PPP, Matrigel, Monostearoyl Glycerol co-Succinate (MGSA), Monostearoyl Glycerol co-Succinate/polyethylene glycol (MGSA/PEG) copolymers, laminin, elastin, hyaluronic acid, proteoglycans, and combinations thereof.

In some embodiments the skeleton can include a reinforcing material. The reinforcing material can be comprised of any absorbable or non-absorbable textile having, for example, woven, knitted, warped knitted (i.e., lace-like), non-woven, and/or braided structures. In one embodiment, the reinforcing material can have a mesh-like structure. Mechanical properties of the material can be altered by changing at least one of the density or texture of the material, the type of knit or weave of the material, the thickness of the material, or by embedding particles in the material. The skeleton can also be made from a braided tube, for instance by cutting it to size and shape curing the edges. The tube can then be heat-set to create the out-of-plane curvature.

Mechanical properties of the reinforcing material can additionally be altered by creating sites within the construct where fibers are physically bonded with each other or physically bonded with another agent, such as, for example, an adhesive or a polymer. The fibers used to make the reinforcing component can be, for example, monofilaments, yarns, threads, braids, or bundles of fibers. These fibers can be made of any biocompatible material including, but not limited to, bioabsorbable materials such as polylactic acid (PLA), polyglycolic acid (PGA), polycaprolactone (PCL), polydioxanone (PDO), trimethylene carbonate (TMC), copolymers or blends thereof. The fibers can also be made from any biocompatible materials based on natural polymers including silk and collagen-based materials. Alternatively, the fibers can also be made of any biocompatible fiber that is nonresorbable, such as, for example, polyethylene, nylon, polyester, polyethylene terephthalate, poly(tetrafluoroethylene), polycarbonate, polypropylene, polyurethane, and poly (vinyl alcohol).

In another embodiment, the construct may incorporate hydroxyapatite, tricalcium phosphate, Bioglass, biphasic calcium phosphate, calcium sulfate, other bone-promoting materials within the whole construct or localized in a portion of the construct where bone regeneration is desired. Bioglass is a silicate containing calcium phosphate glass, or calcium phosphate glass with varying amounts of solid particles added to control resorption time. Bioglass is one example of materials that can be spun into glass fibers and used as a reinforcing material. Bioglass can also be incorporated into the construct in a powder form. Suitable solid particles may be added include iron, magnesium, sodium, potassium, and combinations thereof.

In some embodiments, both the biocompatible construct and the reinforcing material may be formed from a thin, perforation-containing elastomeric sheets with pores or perforations to allow tissue in-growth. A sheet can be made of blends or copolymers of polylactic acid (PLA), polyglycolic acid (PGA), polycaprolactone (PCL), and polydioxanone (PDO).

The construct can be formed at least partially from a polymeric foam component, having pores with an open cell pore structure. The pore size can vary, but preferably, the pores are sized to allow tissue in-growth. In some embodiments, the pore size is approximately in the range of about 40 microns to about 1000 microns, and in other embodiments, the pore size is approximately in the range of about 50 microns to about 500 microns. The polymeric foam component can be made from natural or/and synthetic materials, such as reconstituted collagen. The polymeric foam can be non-crosslinked or crosslinked. The polymeric foam component can, optionally, contain a reinforcing component, such as for example, textiles as discussed above. In some embodiments, the polymeric foam component can contain a reinforcing component which can be integrated with the reinforcing component such that the pores of the foam component penetrate the mesh of the reinforcing component and interlock with the reinforcing component.

In some embodiments the polymeric foam component of the tissue implant may be formed as a foam by a variety of techniques well known to those having skill in the art. For example, the polymeric starting materials may be foamed by lyophilization, supercritical solvent foaming, which is described at least in European Patent Application No. 464, 163, the contents of which is incorporated by reference herein in its entirety, gas injection extrusion, gas injection molding or casting with an extractable material (e.g., salts, sugar, or similar suitable materials).

A polymeric foam component of engineered tissue repair implant devices of the present disclosure may be made by a polymer-solvent phase separation technique, such as lyophilization. A polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution can be separated in a controlled manner into either two distinct phases or two bi-continuous phases. Subsequent removal of the solvent phase usually leaves a porous structure with a density less than the bulk polymer and pores in the micrometer ranges. Additional information about the solvent phase is provided in Microcellular Foams via Phase Separation, J. Vac. Sci. Technol., A. T. Young, Vol. 4(3), May/June 1986, the contents of which is incorporated by reference herein in its entirety.

The steps involved in the preparation of these foams include, for example, choosing the right solvents for the polymers to be lyophilized and preparing a homogeneous solution. Next, the polymer solution can be subjected to a freezing and vacuum drying cycle. The freezing step phase can separate the polymer solution and vacuum drying step can remove the solvent by sublimation and/or drying, leaving a porous polymer structure or an interconnected open cell porous foam. Suitable solvents that may be used in the preparation of the foam component can include, for example, formic acid, ethyl formate, acetic acid, hexafluoroisopropanol (HFIP), cyclic ethers (e.g., tetrahydrofuran (THF), dimethylene fluoride (DMF), and polydioxanone (PDO)), acetone, acetates of C2 to C5 alcohols (e.g., ethyl acetate and t-butylacetate), glyme (e.g., monoglyme, ethyl glyme, diglyme, ethyl diglyme, triglyme, butyl diglyme and tetraglyme), methylethyl ketone, dipropyleneglycol methyl ether, lactones (e.g., γ-valerolactone, δ-valerolactone, γ-butyrolactone, γ-butyrolactone), 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methylpyrrolidone, dimethylformamide, chloroform, 1,2-dichloromethane, morpholine, dimethylsulfoxide, hexafluoroacetone sesquihydrate (HFAS), anisole, and mixtures thereof. Among these solvents, one exemplary solvent is 1,4-dioxane. A homogeneous solution of the polymer in the solvent is prepared using standard techniques.

The applicable polymer concentration or amount of solvent that may be utilized can vary with each system. In one embodiment, the amount of polymer in the solution can vary from about 0.5% to about 90% by weight. In another embodiment, preferably, the amount of polymer in the solution can vary from about 0.5% to about 30% by weight. The amount of polymer in the solution can vary depending on factors such as the solubility of the polymer in a given solvent and the final properties desired in the foam.

In embodiments of the construct that include a polymeric foam, solids may be added to the polymer-solvent system to modify the composition of the resulting polymeric foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting structured tissue augmentation construct, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. In one embodiment, the solids are of a type that will not react with the polymer or the solvent. The added solids can have an average diameter of less than about 2 millimeters. In other embodiments, added solids can have an average diameter of about 50 microns to about 1000 microns. The solids can be present in an amount such that they will constitute from about 1 volume to about 50 volume percent of the total volume of the particle and polymer-solvent mixture (wherein the total volume percent equals 100 volume percent).

Exemplary solids include, for example, particles of demineralized bone, calcium phosphate particles, Bioglass particles, calcium sulfate, or calcium carbonate particles for bone repair, leachable solids for pore creation and particles of bioabsorbable natural polymers, bioabsorbable synthetic polymers, non-bioabsorbable materials, minced extracellular particles, minced tissue fragments, or any biocompatible materials that is not soluble in the solvent system.

Exemplary leachable solids include, for example, non-toxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). Leachable materials can be removed by immersing the foam with the leachable material in a solvent in which the particle is soluble for a sufficient amount of time to allow leaching of substantially all of the particles. The solvent can be chosen so that it does not dissolve or detrimentally alter the foam. One preferred embodiment can include water as the extraction solvent, for example distilled-deionized water. Such a process is described further in U.S. Pat. No. 5,514,378, the contents of which is incorporated by reference herein in its entirety. Preferably the foam will be dried after the leaching process is complete at low temperature and/or vacuum to minimize hydrolysis of the foam unless accelerated absorption of the foam is desired.

Non-bioabsorbable materials can include, for example, bioinert ceramic particles (e.g., alumina, zirconia, and calcium sulfate particles), polymers such as polyethylene, polyvinylacetate, polymethylmethacrylate, polypropylene, poly(ethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., fluoride, polytetrafluoroethylene, and hexafluoropropylene). In one embodiment, it is possible to add solids (e.g., barium sulfate) that will render the tissue implants radio opaque. Those solids that may be added also include those that will promote tissue regeneration or healing, as well as those that act as buffers, reinforcing materials or porosity modifiers.

As discussed above, polymeric foam components can contain a reinforcing component. The construct can be made by injecting, pouring, or otherwise placing, the appropriate polymer solution into a mold set-up comprised of a mold and the reinforcing elements of the present disclosure. The mold set-up can be cooled in an appropriate bath or on a refrigerated shelf and then lyophilized, thereby providing a reinforced construct.

In embodiments that utilize a polymeric foam, one or more of the biological components provided for throughout the present disclosure can be added either before or after the lyophilization step. In the course of forming the polymer foam component, it can be beneficial to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogeneous nucleation occurs. The orientation of the polymeric fibers can be regulated be controlling the pore orientation. The pores orientation in the polymeric form component can be customized, for example, by controlling the temperature gradient induced during the freezing cycle. Controlling the orientation of fibers can result in an improvement in the mechanical properties in the direction that the fibers are oriented.

The required general processing steps for a construct that uses polymeric foam can include the selection of the appropriate materials from which the polymeric foam will be made. The processing steps can additionally include selection of the materials of the reinforcing components if used. If a mesh reinforcing material is used, the proper mesh density should be selected. Further, the reinforcing material should be properly aligned in the mold, the polymer solution should be added at an appropriate rate and, preferably, into a mold that is tilted at an appropriate angle to avoid the formation of air bubbles, and the polymer solution must be lyophilized.

In embodiments that utilize a mesh reinforcing material in a polymeric foam, for example, the reinforcing mesh should be selected to be of a certain density. That is, the openings in the mesh material should not be so small so as to impede proper bonding between the foam and the reinforcing mesh as the foam material and the open cells and cell walls thereof penetrate the mesh openings. Without proper bonding the integrity of the layered structure can be compromised, leaving the construct fragile and difficult to handle. The density of the mesh can determine the mechanical strength of the construct. The density of the mesh can vary according to the desired use for tissue repair. In addition, the type of weave used in the mesh can determine the directionality of the mechanical strength of the construct, as well as the mechanical properties of the reinforcing material, such as for example, the elasticity, stiffness, burst strength, suture retention strength, and ultimate tensile strength of the construct. By way of non-limiting example, the mesh reinforcing material in a foam-based biocompatible construct of the present disclosure can be designed to be stiff in one direction, yet elastic in another, or alternatively, the mesh reinforcing material can be made isotropic.

During lyophilization of the reinforced foam in those embodiments that utilize a mesh reinforcing material in a polymeric foam, several parameters and procedures can be helpful to produce implants with the desired integrity and mechanical properties. For example, if reinforcement material is used, it can be beneficial to maintain the reinforcement material substantially flat when placed in the mold. To ensure the proper degree of flatness, the reinforcement (e.g., mesh) can be pressed flat using a heated press prior to its placement within the mold. Further, in the event that reinforcing structures are not isotropic, it can be desirable to indicate this anisotropy by marking the construct to indicate directionality. The marking can be accomplished by embedding one or more indicators, such as dyed markings or dyed threads, within the woven reinforcements. The direction or orientation of the indicator can, for example, indicate to a surgeon the dimension of the implant in which physical properties are superior.

In embodiments that utilize polymeric foam, as noted above, the manner in which the polymer solution is added to the mold prior to lyophilization can help contribute to the creation of a tissue implant with adequate mechanical integrity. Assuming that a mesh reinforcing material will be used, and that it will be positioned between two thin (e.g., approximately 0.75 millimeters) shims, the mesh can be positioned in a substantially flat orientation at a desired depth in the mold. The polymer solution can be poured in a way that allows air bubbles to escape from between the layers of the foam component. The mold can be tilted at a desired angle and pouring is effected at a controlled rate to best prevent bubble formation. A number of variables will control the tilt angle and pour rate. For example, the mold should be tilted at an angle of greater than about one degree to avoid bubble formation. In addition, the rate of pouring should be slow enough to enable any air bubbles to escape from the mold, rather than to be trapped in the mold.

In those embodiments that utilize a mesh reinforcing material in a polymeric foam, the density of the mesh openings can be an important factor in the formation of the construct with the desired mechanical properties. For example, a low density, or open knitted mesh material, can be used. One example of such a material is a 90:10 copolymer of glycolide and lactide, sold under the tradename VICRYL, which is available from Ethicon, Inc. of Somerville, New Jersey. One exemplary low density, open knitted mesh is Knitted VICRYL VKM-M, which is also available from Ethicon, Inc. of Somerville, New Jersey. Other materials can include but are not limited to polydioxanone and a 95:5 copolymer blend of lactide and glycolide.

In embodiments that utilize a polymeric foam, a through opening can be created by placing a rod in the polymeric foam solution/slurry before it has set. After the polymeric form is formed, the rod can be removed. For example, if the polymeric foam is made by lyophilization, the rod is removed after the freeze and vacuum drying cycle. The rod can have any desired shape.

The polymeric foam component can, optionally, contain one or more layers made of the materials discussed above. In one embodiment, the foam component can be integrated with the material(s) by creating pores in the materials and then the polymeric foam component penetrate the pores created in the materials(s) and interlock with the material(s). In another embodiment, pores are formed in materials of two layers, and the two layers are put together to best align the pores. The two layer combination can be placed in a polymeric solution or slurry, and the polymeric foam can be formed by one of the methods provided for herein or otherwise known to those skilled in the art.

In some embodiments, a construct can be formed from an expanding media that can advantageously provide added compression at the repair site. One non-limiting example of such a construct is disclosed in U.S. patent application Ser. No. 15/419,330, which is incorporated by referenced above.

Unless specified otherwise, any of the materials, and any of the techniques disclosed for forming materials, can be used in conjunction with any of constructs provided for herein. This includes any combination of materials. Likewise, the manufacturing techniques disclosed can generally be used, or adapted to form the various constructs provided for herein. The use of materials and manufacturing techniques for various structured tissue augmentation constructs is within the spirit of the present disclosure.

One skilled in the art will appreciate further features and advantages of the present disclosure based on the above-described embodiments. Accordingly, the disclosure is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A structured surgical construct, comprising
a tissue augmentation block having a first tissue-engaging surface with a surface area defined by a length and a width of the block and a second surface with a surface area defined by the length and the width of the block, the second surface being opposed to the first tissue-engaging surface and a thickness of the block being defined by a distance between the first tissue-engaging surface and the second surface, the surface areas of the first tissue-engaging surface and the second surface being larger than the surface areas of any other sides of the block and the thickness being the shortest of the length, the width, and the thickness of the block; and
a support skeleton at least partially integrated with the tissue augmentation block such that flexing of the tissue augmentation block induces a corresponding flexing of at least a portion of the support skeleton, the support skeleton being configured such that it is biased in an expanded configuration that in turn causes the tissue augmentation block to expand, wherein the support skeleton further comprises:
a spine extending along at least a portion of the length of the block;
a plurality of first ribs extending from the spine along the width of the block in a first direction towards a first end of the block,
a plurality of second ribs extending from the spine along the width of the block in a second direction towards a second end of the block, a distance between the first and second ends defining the width of the block, and
a suture coupled at a first end of the spine and braided around at least a portion of a length of the spine.

2. The structured surgical construct of claim 1, wherein the support skeleton is at least partially encapsulated by the tissue augmentation block.

3. The structured surgical construct of claim 1, wherein the support skeleton comprises a plurality of elements in at least one of a lattice arrangement or a mesh arrangement.

4. The structured surgical construct of claim 1, wherein the plurality of first and second ribs are coupled with the tissue augmentation block such that flexing of the first and second ends of the block about the spine induces a corresponding flexing of the plurality of first and second ribs about the spine.

5. The structured surgical construct of claim 4, wherein the plurality of first and second ribs are curved such that the tissue augmentation block is curved with respect to a longitudinal axis of the spine.

6. The structured surgical construct of claim 4, wherein the first tissue-engaging surface is concave along the length of the tissue augmentation block in the expanded configuration.

7. The structured surgical construct of claim 6, wherein the first tissue-engaging surface can be flexed against a surface to a less concave orientation by applying a force to the spine in a direction towards the surface.

8. The structured surgical construct of claim 4, wherein at least a portion of the plurality of first ribs and at least a portion of the plurality of second ribs extend in non-diametrically opposed directions about a plane perpendicular to the spine such that at least a first lateral portion of the tissue augmentation block is bent about the spine in the plane perpendicular to the spine with respect to a second lateral portion.

9. The structured surgical construct of claim 4, wherein the plurality of first and second ribs are at least one of curved or angled towards a same end of the spine such that the tissue augmentation block is configured to be constricted by deflection of the plurality of first and second ribs towards the spine.

10. The structured surgical construct of claim 1, wherein the support skeleton is made from a bio-absorbable material.

11. The structured surgical construct of claim 1, wherein tissue augmentation block comprises at least one of: fabric, plastic, synthetic polymer, natural polymer, collagen, collagen scaffold, reconstituted collagen, biological autograft connective tissue, biological allograft connective tissue, biological xenograft connective tissue, human dermal matrix, porcine dermal matrix, bovine dermal matrix, periosteal tissue, pericardial tissue, or fascia.

12. The structured surgical construct of claim 11, wherein the tissue augmentation block comprises collagen.

13. The structured surgical construct of claim 1, wherein the support skeleton is monolithic.

14. The structured surgical construct of claim 10, wherein the suture is configured such that, when the spine is absorbed, tension of the suture and association of the suture with the tissue augmentation block is maintained.

15. A surgical kit, comprising
a structured tissue augmentation construct having a first tissue-engaging surface with a surface area defined by a length and a width of the construct and a second surface with a surface area defined by the length and the width of the construct, the second surface being opposed to the first tissue-engaging surface and a thickness of the construct being defined by a distance between the first tissue-engaging surface and the second surface, the surface areas of the first tissue-engaging surface and the second surface being larger than the surface areas of any other sides of the construct and the thickness being the shortest of the length, the width, and the thickness of the construct, the structured tissue augmentation construct including;
a support skeleton at least partially integrated with the tissue augmentation construct such that flexing of the construct induces a corresponding flexing of at least a portion of the support skeleton, the support skeleton being configured such that it is biased in an expanded configuration that in turn causes the structured tissue augmentation construct to expand, wherein the support skeleton comprises a spine extending along at least a portion of the length of the construct, a plurality of first ribs extending from the spine along the width of the construct in a first direction towards a first lateral end of the construct, and a plurality of second ribs extending from the spine along the width of the construct in a second direction towards a second lateral end of the construct; and
a suture coupled at a first end of the spine and braided around at least a portion of a length of the spine, the suture including a first tail configured to extend from a first longitudinal end of the construct and a second tail configured to extend from a second longitudinal end of the construct; and
a delivery tube configured to contain the structured tissue augmentation construct in a constricted arrangement.

16. The surgical kit of claim 15,
wherein the support skeleton further comprises:
a spine extending along at least a portion of the length of the construct;
wherein the plurality of first and second ribs are coupled with the tissue augmentation construct such that flexing of the first and second ends of the construct about the spine induces a corresponding flexing of the plurality of first and second ribs about the spine, and
wherein, in the constricted arrangement, the plurality of first and second ribs are deflected towards the spine.

17. The surgical kit of claim 15, wherein the support skeleton is curved such that the first tissue-engaging surface is concave.

18. A structured surgical construct, comprising:
a tissue augmentation block having a first tissue-engaging surface with a surface area defined by a length and a width of the block and a second surface with a surface area defined by the length and the width of the block, the second surface being opposed to the first tissue-engaging surface and a thickness of the block being defined by a distance between the first tissue-engaging surface and the second surface, the surface areas of the first tissue-engaging surface and the second surface being larger than the surface areas of any other sides of the block and the thickness being the shortest of the length, the width, and the thickness of the block; and
a support skeleton at least partially integrated with the tissue augmentation block such that flexing of the tissue augmentation block induces a corresponding flexing of at least a portion of the support skeleton, the support skeleton being configured such that it is biased in an expanded configuration that in turn causes the tissue augmentation block to expand, wherein the support skeleton further comprises:
a spine extending along at least a portion of the length of the block;
a plurality of first support elements extending from the spine along the width of the block in a first direction towards a first end of the block;
a plurality of second support elements extending from the spine along the width of the block in a second direction towards a second end of the block, a distance between the first and second ends defining the width of the block, and
a suture braided around the spine.

19. The structured surgical construct of claim 18, wherein the support skeleton comprises a plurality of elements in at least one of a lattice arrangement or a mesh arrangement.

* * * * *